(12) United States Patent
Idusogie et al.

(10) Patent No.: US 6,528,624 B1
(45) Date of Patent: *Mar. 4, 2003

(54) POLYPEPTIDE VARIANTS

(75) Inventors: Esohe Ekinaduese Idusogie, Burlingame, CA (US); Leonard G. Presta, San Francisco, CA (US); Michael George Mulkerrin, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/282,846

(22) Filed: Mar. 31, 1999

Related U.S. Application Data

(60) Provisional application No. 60/080,447, filed on Apr. 2, 1998, and provisional application No. 60/116,100, filed on Jan. 15, 1999.

(51) Int. Cl.[7] ............................................... C12P 21/08
(52) U.S. Cl. .............................. 530/387.3; 424/142.1; 435/328
(58) Field of Search ...................... 435/328; 424/142.1; 530/387.3, 387.1

(56) References Cited

U.S. PATENT DOCUMENTS

| | | |
|---|---|---|
| 4,752,601 A | 6/1988 | Hahn |
| 5,348,876 A | 9/1994 | Michaelsen et al. |
| 5,624,821 A | 4/1997 | Winter et al. |
| 5,648,260 A | 7/1997 | Winter et al. |
| 5,698,449 A | 12/1997 | Baumann et al. |
| 5,736,137 A | 4/1998 | Anderson et al. |

FOREIGN PATENT DOCUMENTS

| | | |
|---|---|---|
| WO | WO 88/07089 | 9/1988 |
| WO | WO 94/29351 | 12/1994 |
| WO | WO 97/28267 | 8/1997 |
| WO | WO 97/44362 | 11/1997 |
| WO | WO 98/23289 | 6/1998 |
| WO | WO 98/52975 | 11/1998 |
| WO | WO 99/43713 | 9/1999 |
| WO | WO 99/51642 | 10/1999 |
| WO | WO 99/58572 | 11/1999 |
| WO | WO 00/09560 | 2/2000 |

OTHER PUBLICATIONS

Armour et al., "Recombinant human IgG–molecules lacking Fcγ receptor I binding and monocyte triggering activities" *European Journal of Immunology* 29(8):2613–2624 (Aug. 1999).

Jaakkola et al., "In Vivo detection of vascular adhesion protein–1 in experimental inflammation" *American Journal of Pathology* 157(2):463–471 (Aug. 2000).

Alistair et al., "Participation of the N–terminal region of Cepsilon3 in the binding of human IgE to its high–affinity receptor FcepsilonRI" *Biochemistry* (abstract only) 36:15568–15578 (1997).

Medesan et al., "Comparative studies of rat IgG to further delineate the Fc:FcRN interaction site" *European Journal of Immunology* 28:2092–2100 (1998).

Janeway et al. *Immunobiology, The Immune System in Health and Disease*, CB Ltd and Garland Publishing Inc., NY & London (1994), pp. 3:29 & 3:30.

Burmeister et al., "Crystal structure of the complex of rat neonatal Fc receptor with Fc" *Nature* 372:379–383 (Nov. 24, 1994).

Carter et al., "Humanization of an anti–p185$^{HER2}$ antibody for human cancer therapy" *Proc. Natl. Acad. Sci.* 89:4285–4289 (May 1992).

Duncan et al., "Localization of the binding site for the human high–affinity FC receptor on IgG" *Nature* 332:563–564 (Apr. 7, 1988).

Gergely et al., "Fc receptors on lymphocytes and K cells" *Biochemical Society Transactions* 12(5):739–743 (Oct. 1984).

Ghetie and Ward, "FcRn: the MHC class I–related receptor that is more than an IgG transporter" *Immunology Today* 18(12):592–598 (Dec. 1997).

Ghetie et al., "Abnormally short serum half–lives of IgG in β2–microglobulin–deficient mice" *European Journal of Immunology* 26(3):690–696 (Mar. 1996).

Ghetie et al., "Increasing the serum persistence of an IgG fragment by random mutagenesis" *Nature Biotechnology* 15(7):637–640 (Jul. 1997).

Greenwood et al., "Structural motifs involved in human IgG antibody effector functions" *European Journal of Immunology* 23(5):1098–1104 (May 1993).

Hadley et al., "The functional activity of FcγRII and FcγRIII on subsets of human lymphocytes" *Immunology* 76(3):446–451 (Jul. 1992).

Kim et al., "Catabolism of the Murine IgG1 Molecule: Evidence That Both CH2–CH3 Domain Interfaces are Required for Persistence of IgG1 in the Circulation of Mice" *Scandinavian Journal Of Immunology* 40(4):457–465 (1994).

Kim et al., "Identifying amino acid residues that influence plasma clearance of murine IgG1 fragments by site–directed mutagenesis" *European Journal of Immunology* 24:542–548 (1994).

(List continued on next page.)

Primary Examiner—Patrick J. Nolan
(74) Attorney, Agent, or Firm—Wendy M. Lee

(57) ABSTRACT

A variant of a polypeptide comprising a human IgG Fc region is described, which variant comprises an amino acid substitution at one or more of amino acid positions 270, 322, 326, 327, 329, 331, 333 or 334 of the human IgG Fc region. Such variants display altered effector function. For example, C1q binding and/or complement dependent cytotoxicity (CDC) activity may be altered in the variant polypeptide. The application also discloses a variant of a parent polypeptide comprising a human IgG Fc region, which variant has a better binding affinity for human C1q than the parent polypeptide.

20 Claims, 12 Drawing Sheets

OTHER PUBLICATIONS

Lehrnbecher et al., "Variant genotypes of the low–affinity Fcγ receptors in two control populations and a review of low–affinity Fcγ receptor polymorphisms in control and disease populations" *Blood* 94(12):4220–4232 (Dec. 15, 1999).

Lorenz et al., "Strong association between the responder status of the FCγII receptor and recurrent spontaneous abortion" *European Journal of Immunogenetics* 22(5):397–401 (Oct. 1995).

Medesan et al., "Delineation of the amino acid residues involved in transcytosis and catabolism of mouse IgG1" *Journal of Immunology* 158(5):2211–2217 (Mar. 1, 1997).

Medesan et al., "Localization of the site of the IgG molecule that regulates maternofetal transmission in mice" *European Journal of Immunology* 26(10):2533–2536 (Oct. 1996).

Popov et al., "The stoichiometry and affinity of the interaction of murine Fc fragments with the MHC class I–related receptor, FcRn" *Molecular Immunology* 33(6):521–530 (Apr. 1996).

Raghavan et al., "Analysis of the pH dependence of the neonatal Fc receptor/immunoglobulin G interaction using antibody and receptor variants" *Biochemistry* 34(45):14649–14657 (Nov. 14, 1995).

Ravetch and Clynes, "Divergent roles for Fc receptors and complement in vivo" *Annual Review of Immunology* 16:421–432 (1998).

Sarmay et al., "Ligand inhibition studies on the role of Fc receptors in antibody–dependent cell–mediated cytotoxicity" *Molecular Immunology* 21(1):43–51 (Jan. 1984).

Ting et al., "Fcγ receptor activation induces the tyrosine phosphorylation of both phospholipase C (PLC)–γ1 and PLC–γ2 in natural killer cells" *Journal of Experimental Medicine* 176(6):1751–1755 (Dec. 1, 1992).

Vance et al., "Binding of monomeric human IgG defines an expression polymorphism of FcγRIII on large granular lymphocyte/natural killer cells" *Journal of Immunology* 151(11):6429–6439 (Dec. 1, 1993).

Weng et al., "Computational determination of the structure of rat Fc bound to the neonatal Fc receptor" *Journal of Molecular Biology* 282(2):217–225 (Sep. 18, 1998).

Woof et al., "Localisation of the monocyte–binding region on human immunoglobulin G" *Molecular Immunology* 23(3):319–330 (Mar. 1986).

Wu et al., "A novel polymorphism of FcγRIIIa (CD16) alters receptor function and predisposes to autoimmune disease" *Journal of Clinical Investigation* 100(5):1059–1070 (Sep. 1, 1997).

Yap et al., "Human Fc gamma receptor IIA (FcγRIIA) genotyping and association with systemic lupus erythematosus (SLE) in Chinese and Malays in Malaysia" *Lupus* 8(4):305–310 (1999).

Huizinga et al, "Binding Characteristics of Dimeric IgG Subclass Complexes to Human Neutrophils" *Journal of Immunology* 142:2359–2364 (1989).

Ngo et al., "Computational Complexity, Protein Structure Prediction, and the Levinthal Paradox" *The Protein Folding Problem and Tertiary Structure Prediction*, Merz & Le Grand, Boston:Birkhauser pp. 491–495 (1994).

Allan and Isliker, "Studies on the complement–binding site of rabbit immunoglobulin G–I. Modification of tryptophan residues and their role in anticomplementary activity of rabbit IgG" *Immunochemistry* 11(4):175–180 (Apr. 1974).

Angal et al., "A single amino acid substitution abolishes the heterogeneity of chimeric mouse/human (IgG4) antibody" *Molecular Immunology* 30(1):105–108 (Jan. 1993).

Bloom et al., "Intrachain disulfide bond in the core hinge region of human IgG4" *Protein Science* 6:407–415 (1997).

Bredius et al., "Role of neutrophil FcγRIIa (CD32) and FcγRIIIb (CD16) polymorphic forms in phagocytosis of human IgG1– and IgG3–opsonized bacteria and erythrocytes" *Immunology* 83(4):624–630 (Dec. 1994).

Brekke et al., "Human IgG isotype–specific amino acid residues affecting complement–mediated cell lysis and phagocytosis" *European Journal of Immunology* 24(10):2542–2547 (Oct. 1994).

Burton and Woof, "Human Antibody Effector Function" *Advances in Immunology* 51:1–84 (1992).

Burton et al., "The Clq receptor site on immunoglobulin G" *Nature* 288(5789):338–344 (Nov. 27, 1980).

Burton, "Immunoglobulin G: Functional Sites" *Molecular Immunology* 22(3):161–206 (1985).

Canfield and Morrison, "The binding affinity of human IgG for its high affinity Fc receptor is determined by multiple amino acids in the $C_H2$ domain and is modulated by the hinge region" *Journal of Experimental Medicine* 173(6):1483–1491 (Jun. 1, 1991).

Capel et al., "Heterogeneity of Human IgG Fc Receptors" *Immunomethods* 4:25–34 (1994).

Chappel et al., "Identification of the Fcγ receptor class I binding site in human IgG through the use of recombinant IgG1/IgG2 hybrid and point–mutated antibodies" *Proc. Natl. Acad. Sci. USA* 88(20):9036–9040 (Oct. 15, 1991).

Cosimi, "Clinical Development of Orthoclone OKT3" *Transplantation Proceedings* (Suppl 1) XIX(2):7–16 (Apr. 1987).

Daeron, M., "Fc Receptor Biology" *Annual Review of Immunology* 15:203–234 (1997).

de Haas et al., "Fcγ receptors of phagocytes" *J. of Laboratory Clinical Medicine* 126:330–341 (1995).

Deisenhofer, "Crystallographic Refinement and Atomic Models of a Human Fc fragment and Its Complex with Fragment B of Protein A from *Staphylococcus aureus* at 2.9– and 2.8–A Resolution" *Biochemistry* 20(9):2361–2370 (1981).

Duncan and Winter, "The binding site for Clq on IgG" *Nature* 332:738–740 (Apr. 21, 1988).

Gazzano–Santoro et al., "A non–radioactive complement-dependent cytotoxicity assay for anti–CD20 monoclonal antibody" *Journal of Immunological Methods* 202:163–171 (1997).

Ghebrehiwet et al., "Isolation, cDNA cloning, and overexpression of a 33–kD cell surface glycoprotein that binds to the globular "heads" of Clq" *Journal of Experimental Medicine* 179(6):1809–1821 (Jun. 1, 1994).

Gorman et al., "Transient Production of Proteins Using an Adenovirus Transformed Cell Line" *DNA Prot. Eng. Tech.* 2(1):3–10 (1990).

Graham et al., "Characteristics of a Human Cell Line Transformed by DNA from Human Adenovirus Type 5" *J. Gen. Virol.* 36:59–72 (1977).

Greenwood et al., "Engineering multiple–domain forms of the therapeutic antibody CAMPATH–1H: effects on complement lysis" *Therapeutic Immunology* 1(5):247–255 (Oct. 1994).

Hogarth et al., "Characterization of FcR Ig–binding sites and epitope mapping" *Immunomethods* 4(1):17–24 (Feb. 1994).

Jefferis et al., "Molecular Definition of Interaction Sites on Human IgG for Fc Receptors (huFcγR)" *Molecular Immunology* 27(12):1237–1240 (1990).

Kabat, E. et al. *Sequences of Proteins of Immunological Interest* (pp. 669, 671, 687, 696), 5th edition, Bethesda, MD:NIH vol. 1 (1991).

Kim et al., "Localization of the site of the murine IgG1 molecule that is involved in binding to the murine intestinal Fc receptor" *European Journal of Immunology* 24:2429–2434 (1994).

Kunkel, T., "Rapid and Efficient Site–Specific Mutagenesis Without Phenotypic Selection" *Proc. Natl. Acad. Sci.* 82:488–492 (1985).

Lauvrak et al., "Identification and characterization of C1q–binding phage displayed peptides" *Biological Chemistry* 378(12):1509–1519 (Dec. 1997).

Lund et al., "Human FcγRI and Fcγ RII interact with distinct but overlapping sites on human IgG" *Journal of Immunology* 147(8):2657–2662 (Oct. 15, 1991).

Lund et al., "Multiple binding sites on the $C_H2$ domain of IgG for mouse FcγR11" *Molecular Immunology* 29(1):53–59 (Jan. 1992).

Morgan et al., "The N–terminal end of the $C_H2$ domain of chimeric human IgG1 anti–HLA–DR is necessary for C1q, FcγRI and FCγRIII binding" *Immunology* 86(2):319–324 (Oct. 1995).

Morrison et al., "Structural Determinants of Human IgG Function" *Immunologist* 2:119–124 (1994).

Nagarajan et al., "Ligand binding and phagocytosis by CD16 (Fc γ receptor III) isoforms. Phagocytic signaling by associated ζ and γ subunits in Chinese hamster ovary cells" *Journal of Biological Chemistry* 270(43):25762–25770 (Oct. 27, 1995).

Presta et al., "Humanization of an Anti–Vascular Endothelial Growth Factor Monoclonal Antibody for the Therapy of Solid Tumors and Other Disorders" *Cancer Research* 57(20):4593–4599 (Oct. 15, 1997).

Ravetch and Kinet, "Fc Receptors" *Annual Review of Immunology* 9:457–492 (1991).

Reff et al., "Depletion of B cells in vivo by a chimeric mouse human monoclonal antibody to CD20" *Blood* 83(2):435–445 (Jan. 15, 1994).

Sarmay et al., "Mapping and comparison of the interaction sites on the Fc region of IgG responsible for triggering antibody dependent cellular cytotoxicity (ADCC) through different types of human Fcγ receptor" *Molecular Immunology* 29(5):633–639 (May 1992).

Sensel et al., "Amino acid differences in the N–terminus of $C_H2$ influence the relative abilities of IgG2 and IgG3 to activate complement" *Molecular Immunology* 34(14):1019–1029 (Oct. 1997).

Strohmeier et al., "Neutrophil functional responses depend on immune complex valency" *Journal of Leukocyte Biology* 58(4):403–414 (Oct. 1995).

Strohmeier et al., "Role of the FcγR subclasses FcγRIII and FcγRIII in the activation of human neutrophils by low and high valency immune complexes" *Journal of Leukocyte Biology* 58(4):415–422 (Oct. 1995).

Tamm et al., "The IgG binding site of human FcγRIIIB receptor involves CC' and FG loops of the membrane–proximal domain" *Journal of Biological Chemistry* 271(7):3659–3666 (Feb. 16, 1996).

Tao et al., "Structural features of human immunoglobulin G that determine isotype–specific differences in complement activation" *Journal of Experimental Medicine* 178(2):661–667 (Aug. 1, 1993).

Tao et al., "Studies of aglycosylated chimeric mouse–human IgG. Role of Carbohydrate in the Structure and Effector Functions Mediated by the Human IgG Constant Region" *Journal of Immunology* 143(8):2595–2601 (Oct. 15, 1989).

Tao et al., "The differential ability of human IgG1 and IgG4 to activate complement is determined by the COOH–terminal sequence of the $C_H2$ domain" *Journal of Experimental Medicine* 173(4):1025–1028 (Apr. 1991).

Tax et al., "Fc receptors for mouse IgG1 on human monocytes: polymorphism and role in antibody–induced T cell proliferation" *Journal of Immunology* 133(3):1185–1189 (Sep. 1984).

Urfer et al., "High resolution mapping of the binding site of TrkA for nerve growth factor and TrkC for neurotrophin–3 on the second immunoglobulin–like domain of the Trk receptors" *Journal of Biological Chemistry* 273(10):5829–5840 (Mar. 6, 1998).

Van de Winkel and Anderson, "Biology of human immunoglobulin G Fc receptors" *Journal of Leukocyte Biology* 49(5):511–524 (May 1991).

Ward and Ghetie, "The effector functions of immunoglobulins: implications for therapy" *Therapeutic Immunology* 2(2):77–94 (Apr. 1995).

Warmerdam et al., "A single amino acid in the second Ig–like domain of the human Fcγ receptor II is critical for human IgG2 binding" *Journal of Immunology* 147(4):1338–1343 (Aug. 15, 1991).

Werther et al., "Humanization of an Anti–Lymphocyte Function–Associated Antigen (LFA)–1 Monoclonal Antibody and Reengineering of the Humanized Antibody for Binding to Rhesus LFA–1" *J. of Immunology* 157:4986–4995 (1996).

Wright and Morrison, "Effect of altered $C_H2$–associated carbohydrate structure on the functional properties and in vivo fate of chimeric mouse–human immunoglobulin G1" *Journal of Experimental Medicine* 180(3):1087–1096 (Sep. 1, 1994).

Xu et al., "The N–terminal sequence of the $C_H2$ domain controls the differential ability of human IgG1 and IgG2 to activate complement" *Journal of Immunology* (abstract No. 862) 150(8):152A (Apr. 15, 1993).

FIG. 4A    (E27) - Light Chain

```
DIQLTQSPSS LSASVGDRVT ITCRASKPVD GEGDSYMNWY QQKPGKAPKL LIYAASYLES GVPSRFSGSG
SGTDFTLTIS SLQPEDFATY YCQQSHEDPY TFGQGTKVEI KRTVAAPSVF IFPPSDEQLK SGTASVVCLL
NNFYPREAKV QWKVDNALQS GNSQESVTEQ DSKDSTYSLS STLTLSKADY EKHKVYACEV THQGLSSPVT
KSFNRGEC
```

FIG. 4B    (E27) - Heavy Chain

```
EVQLVESGGG LVQPGGSLRL SCAVSGYSIT SGYSWNWIRQ APGKGLEWVA SIKYSGETKY NPSVKGRITI
SRDDSKNTFY LQMNSLRAED TAVYYCARGS HYFGHWHFAV WGQGTLVTVS SASTKGPSVF PLAPSSKSTS
GGTAALGCLV KDYFPEPVTV SWNSGALTSG VHTFPAVLQS SGLYSLSSVV TVPSSSLGTQ TYICNVNHKP
SNTKVDKKVE PKSCDKTHTC PPCPAPELLG GPSVFLFPPK PKDTLMISRT PEVTCVVVDV SHEDPEVKFN
WYVDGVEVHN AKTKPREEQY NSTYRVVSVL TVLHQDWLNG KEYKCKVSNK ALPAPIEKTI SKAKGQPREP
QVYTLPPSRE EMTKNQVSLT CLVKGFYPSD IAVEWESNGQ PENNYKTTPP VLDSDGSFFL YSKLTVDKSR
WQQGNVFSCS VMHEALHNHY TQKSLSLSPG K
```

SEQUENCE LISTING

<160> NUMBER OF SEQ ID NOS: 2

<210> SEQ ID NO 1
<211> LENGTH: 218
<212> TYPE: PRT
<213> ORGANISM: Artificial Sequence
<220> FEATURE:
<221> NAME/KEY: Artificial Sequence
<222> LOCATION: 1-218
<223> OTHER INFORMATION: Sequence is completely synthesized

<400> SEQUENCE: 1

```
Asp Ile Gln Leu Thr Gln Ser Pro Ser Ser Leu Ser Ala Ser Val
 1               5                  10                  15

Gly Asp Arg Val Thr Ile Thr Cys Arg Ala Ser Lys Pro Val Asp
                20                  25                  30

Gly Glu Gly Asp Ser Tyr Met Asn Trp Tyr Gln Gln Lys Pro Gly
                35                  40                  45

Lys Ala Pro Lys Leu Leu Ile Tyr Ala Ala Ser Tyr Leu Glu Ser
                50                  55                  60

Gly Val Pro Ser Arg Phe Ser Gly Ser Gly Ser Gly Thr Asp Phe
                65                  70                  75

Thr Leu Thr Ile Ser Ser Leu Gln Pro Glu Asp Phe Ala Thr Tyr
                80                  85                  90

Tyr Cys Gln Gln Ser His Glu Asp Pro Tyr Thr Phe Gly Gln Gly
                95                  100                 105

Thr Lys Val Glu Ile Lys Arg Thr Val Ala Ala Pro Ser Val Phe
                110                 115                 120

Ile Phe Pro Pro Ser Asp Glu Gln Leu Lys Ser Gly Thr Ala Ser
                125                 130                 135

Val Val Cys Leu Leu Asn Asn Phe Tyr Pro Arg Glu Ala Lys Val
                140                 145                 150

Gln Trp Lys Val Asp Asn Ala Leu Gln Ser Gly Asn Ser Gln Glu
                155                 160                 165

Ser Val Thr Glu Gln Asp Ser Lys Asp Ser Thr Tyr Ser Leu Ser
                170                 175                 180

Ser Thr Leu Thr Leu Ser Lys Ala Asp Tyr Glu Lys His Lys Val
                185                 190                 195

Tyr Ala Cys Glu Val Thr His Gln Gly Leu Ser Ser Pro Val Thr
                200                 205                 210

Lys Ser Phe Asn Arg Gly Glu Cys
                215         218
```

<210> SEQ ID NO 2
<211> LENGTH: 451
<212> TYPE: PRT
<213> ORGANISM: Artificial Sequence
<220> FEATURE:
<221> NAME/KEY: Artificial Sequence
<222> LOCATION: 1-451
<223> OTHER INFORMATION: Sequence is completely synthesized

<400> SEQUENCE: 2

-continued

```
Glu Val Gln Leu Val Glu Ser Gly Gly Gly Leu Val Gln Pro Gly
  1               5                  10                  15
Gly Ser Leu Arg Leu Ser Cys Ala Val Ser Gly Tyr Ser Ile Thr
                 20                  25                  30
Ser Gly Tyr Ser Trp Asn Trp Ile Arg Gln Ala Pro Gly Lys Gly
                 35                  40                  45
Leu Glu Trp Val Ala Ser Ile Lys Tyr Ser Gly Glu Thr Lys Tyr
                 50                  55                  60
Asn Pro Ser Val Lys Gly Arg Ile Thr Ile Ser Arg Asp Asp Ser
                 65                  70                  75
Lys Asn Thr Phe Tyr Leu Gln Met Asn Ser Leu Arg Ala Glu Asp
                 80                  85                  90
Thr Ala Val Tyr Tyr Cys Ala Arg Gly Ser His Tyr Phe Gly His
                 95                 100                 105
Trp His Phe Ala Val Trp Gly Gln Gly Thr Leu Val Thr Val Ser
                110                 115                 120
Ser Ala Ser Thr Lys Gly Pro Ser Val Phe Pro Leu Ala Pro Ser
                125                 130                 135
Ser Lys Ser Thr Ser Gly Gly Thr Ala Ala Leu Gly Cys Leu Val
                140                 145                 150
Lys Asp Tyr Phe Pro Glu Pro Val Thr Val Ser Trp Asn Ser Gly
                155                 160                 165
Ala Leu Thr Ser Gly Val His Thr Phe Pro Ala Val Leu Gln Ser
                170                 175                 180
Ser Gly Leu Tyr Ser Leu Ser Ser Val Val Thr Val Pro Ser Ser
                185                 190                 195
Ser Leu Gly Thr Gln Thr Tyr Ile Cys Asn Val Asn His Lys Pro
                200                 205                 210
Ser Asn Thr Lys Val Asp Lys Lys Val Glu Pro Lys Ser Cys Asp
                215                 220                 225
Lys Thr His Thr Cys Pro Pro Cys Pro Ala Pro Glu Leu Leu Gly
                230                 235                 240
Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val
                260                 265                 270
Ser His Glu Asp Pro Glu Val Lys Phe Asn Trp Tyr Val Asp Gly
                275                 280                 285
Val Glu Val His Asn Ala Lys Thr Lys Pro Arg Glu Glu Gln Tyr
                290                 295                 300
Asn Ser Thr Tyr Arg Val Val Ser Val Leu Thr Val Leu His Gln
                305                 310                 315
Asp Trp Leu Asn Gly Lys Glu Tyr Lys Cys Lys Val Ser Asn Lys
                320                 325                 330
Ala Leu Pro Ala Pro Ile Glu Lys Thr Ile Ser Lys Ala Lys Gly
                335                 340                 345
Gln Pro Arg Glu Pro Gln Val Tyr Thr Leu Pro Pro Ser Arg Glu
                350                 355                 360
Glu Met Thr Lys Asn Gln Val Ser Leu Thr Cys Leu Val Lys Gly
                365                 370                 375
Phe Tyr Pro Ser Asp Ile Ala Val Glu Trp Glu Ser Asn Gly Gln
                380                 385                 390
```

-continued

```
Pro Glu Asn Asn Tyr Lys Thr Thr Pro Pro Val Leu Asp Ser Asp
                395                 400                 405

Gly Ser Phe Phe Leu Tyr Ser Lys Leu Thr Val Asp Lys Ser Arg
                410                 415                 420

Trp Gln Gln Gly Asn Val Phe Ser Cys Ser Val Met His Glu Ala
                425                 430                 435

Leu His Asn His Tyr Thr Gln Lys Ser Leu Ser Leu Ser Pro Gly
                440                 445                 450

Lys
451
```

US 6,528,624 B1

POLYPEPTIDE VARIANTS

This is a non-provisional application claiming priority under 35 USC §119 to provisional application No. 60/080,447 filed Apr. 2, 1998 and provisional application No. 60/116,100 filed Jan. 15, 1999, the entire disclosures of which are hereby incorporated by reference.

BACKGROUND OF THE INVENTION

1. Field of the Invention

The present invention concerns variants of polypeptides comprising an Fc region. More particularly, the present invention concerns Fc region-containing polypeptides that have altered effector function as a consequence of one or more amino acid substitutions in the Fc region of the nonvariant polypeptide. The invention also relates to novel immune complexes and an assay for determining binding of an analyte, such as an Fc region-containing polypeptide, to a receptor.

2. Description of Related Art

Antibodies are proteins, which exhibit binding specificity to a specific antigen. Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in three segments called complementarity determining regions (CDRs) both in the light chain and the heavy chain variable domains. The more highly conserved portions of the variable domains are called the framework regions (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al., *Sequences of Proteins of Immunological Interest*, 5th Ed. Public Health Service, National Institutes of Health, Bethesda, Md. (1991)).

The constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and several of these may be further divided into subclasses (isotypes), e.g. IgG1, IgG2, IgG3, and IgG4; IgA1 and IgA2. The heavy chain constant regions that correspond to the different classes of immunoglobulins are called α, δ, ε, γ, and μ, respectively. Of the various human immunoglobulin classes, only human IgG1, IgG2, IgG3 and IgM are known to activate complement.

A schematic representation of the native IgG1 structure is shown in FIG. 1, where the various portions of the native antibody molecule are indicated. Papain digestion of antibodies produces two identical antigen binding fragments, called Fab fragments, each with a single antigen binding site, and a residual "Fc" fragment, whose name reflects its ability to crystallize readily. The crystal structure of the human IgG Fc region has been determined (Deisenhofer, *Biochemistry* 20:2361–2370 (1981)). In human IgG molecules the Fc region is generated by papain cleavage N-terminal to Cys 226. The Fc region is central to the effector functions of antibodies.

The effector functions mediated by the antibody Fc region can be divided into two categories: (1) effector functions that operate after the binding of antibody to an antigen (these functions involve the participation of the complement cascade or Fc receptor (FcR)-bearing cells); and (2) effector functions that operate independently of antigen binding (these functions confer persistence in the circulation and the ability to be transferred across cellular barriers by transcytosis). Ward and Ghetie, *Therapeutic Immunology* 2:77–94 (1995).

While binding of an antibody to the requisite antigen has a neutralizing effect that might prevent the binding of a foreign antigen to its endogenous target (e.g. receptor or ligand), binding alone may not remove the foreign antigen. To be efficient in removing and/or destructing foreign antigens, an antibody should be endowed with both high affinity binding to its antigen, and efficient effector functions.

C1q Binding

C1q and two serine proteases, C1r and C1s, form the complex C1, the first component of the complement dependent cytotoxicity (CDC) pathway. C1q is a hexavalent molecule with a molecular weight of approximately 460,000 and a structure likened to a bouquet of tulips in which six collagenous "stalks" are connected to six globular head regions. Burton and Woof, *Advances in Immunol* 51:1–84 (1992). To activate the complement cascade, it is necessary for C1q to bind to at least two molecules of IgG1, IgG2, or IgG3 (the consensus is that IgG4 does not activate complement), but only one molecule of IgM, attached to the antigenic target. Ward and Ghetie, *Therapeutic Immunology* 2:77–94 (1995) at page 80.

Based upon the results of chemical modifications and crystallographic studies, Burton et al. (*Nature*, 288:338–344 (1980)) proposed that the binding site for the complement subcomponent C1q on IgG involves the last two (C-terminal) β-strands of the CH2 domain. Burton later suggested (Molec. *Immunol.*, 22(3):161–206 (1985)) that the region comprising amino acid residues 318 to 337 might be involved in complement fixation.

Duncan and Winter (*Nature* 332:738–40 (1988)), using site directed mutagenesis, reported that Glu318, Lys320 and Lys322 form the binding site to C1q. The data of Duncan and Winter were generated by testing the binding of a mouse IgG2b isotype to guinea pig C1q. The role of Glu318, Lys320 and Lys322 residues in the binding of C1q was confirmed by the ability of a short synthetic peptide containing these residues to inhibit complement mediated lysis.

Similar results are disclosed in U.S. Pat. No. 5,648,260 issued on Jul. 15, 1997, and U.S. Pat. No. 5,624,821 issued on Apr. 29, 1997.

The residue Pro331 has been implicated in C1q binding by analysis of the ability of human IgG subclasses to carry out complement mediated cell lysis. Mutation of Ser331 to Pro331 in IgG4 conferred the ability to activate complement. (Tao et al., *J. Exp. Med.*, 178:661–667 (1993); Brekke et al., *Eur. J. Immunol.*, 24:2542–47 (1994)).

From the comparison of the data of the Winter group, and the Tao et aL and Brekke et aL papers, Ward and Ghetie concluded in their review article that there are at least two different regions involved in the binding of C1q: one on the β-strand of the CH2 domain bearing the Glu318, Lys320 and Lys322 residues, and the other on a turn located in close proximity to the same β-strand, and containing a key amino acid residue at position 331.

Other reports suggested that human IgG1 residues Lys235, and Gly237, located in the lower hinge region, play a critical role in complement fixation and activation. Xu et al.,*J. Immunol.* 150:1 52A (Abstract) (1993). WO94/29351 published Dec. 22, 1994 reports that amino acid residues necessary for C1q and FcR binding of human IgG1 are located in the N-terminal region of the CH2 domain, i.e. residues 231 to 238.

It has further been proposed that the ability of IgG to bind C1q and activate the complement cascade also depends on the presence, absence or modification of the carbohydrate moiety positioned between the two CH2 domains (which is normally anchored at Asn297). Ward and Ghetie, *Therapeutic Immunology* 2:77–94 (1995) at page 81.

Fc Receptor Binding

Effector functions can also be mediated by the interaction of the Fc region of an antibody with Fc receptors (FcRs), which are specialized cell surface receptors on hematopoietic cells. Fc receptors belong in the immunoglobulin superfamily, and have been shown to mediate both the removal of antibody-coated pathogens by phagocytosis of immune complexes, and the lysing of erythrocytes and various other cellular targets (e.g. tumor cells) coated with the corresponding antibody, via antibody dependent cell mediated cytotoxicity (ADCC). Van de Winkel and Anderson, *J. Leuk. Biol.* 49:511–24 (1991).

FcRs are defined by their specificity for immunoglobulin isotypes; Fc receptors for IgG antibodies are referred to as FcγR, for IgE as FcϴR, for IgA as FcαR and so on. Three subclasses of gamma receptors have been identified: FcγRI (CD64), FeγRII (CD32) and FcγRII (CD16). Because each FcγR subclass is encoded by two or three genes, and alternative RNA spicing leads to multiple transcripts, a broad diversity in FcγR isoforms exists. The three genes encoding the FcγRI subclass (FcγRIA, FcγRIB and FcγRIC) are clustered in region 1q21.1 of the long arm of chromosome 1; the genes encoding FcγRII isoforms (FcγRIIA, FcγRIIB and FcγRIIC) and the two genes encoding FcγRIII (FcγRIIIA and FcγRIIIB) are all clustered in region 1q22. FcRs are reviewed in Ravetch and Kinet, *Annu. Rev. Immunol* 9:457–92 (1991); Capel et al., *Immunomethods* 4:25–34 (1994); and de Haas et al., *J. Lab. Clin. Med.* 126:330–41 (1995).

While FcγRI binds monomeric IgG with a high affinity, FcγRII and FcγRIII are low-affinity receptors, interacting with complexed or aggregated IgG. The classical method for detecting these low-affinity receptors is by "rosetting" using antibody-coated erythrocytes (EA) sensitized with IgGs. Bredius et al. evaluated rosette formation between IgG-sensitized red blood cells and polymorphonuclear leukocytes (PMN) which express FcγγIIa and FcγRIIIb at their cell-surface. Rosette was defined as three of more EA bound per PMN (Bredius et al. *Immunology* 83:624–630 (1994)). See, also, Tax et al. *J. Immunol.* 133(3):1185–1189 (1984); Nagarajan et al. *J. Biol Chem.* 270(43):25762–25770 (1995); and Warmerdam et al. *J. Immunol.* 147(4):1338–1343 (1991) concerning rosette assays. However, binding of these EA "immune complexes" to FcR is not easily quantified. Accordingly, more defined complexes with detectable affinity for these FcRs have been developed. For example, IgG dimers have been formed using anti-light chain monoclonal antibodies (Nagarajan et al., supra and Warmerdam et aL, supra) or chemical cross-linking agents (Hogarth et al. *Immunomethods* 4:17–24 (1994); and Tamm et al. J. Biol. Chem. 271(7):3659–3666(1996)). Heat-aggregated immune complexes have also been evaluated for binding to cells expressing FcRs (Tax et aL, supra and Tam et al., supra).

The binding site for the FcγRs on human IgG was found to reside in the lower hinge region, primarily involving residues at amino acid positions 233–238, all of which were found to be necessary for full FcγR binding activity. Canfield and Morrison,*J. Exp. Med.* 173:1483–91 (1991); Chappel et al., *Proc. Nati. Acad. Sci. USA*, 88:9036–40 (1991); Lund et al., *J. Immunol.*, 147:2657–62 (1991); Lund et al., *Molec. Immunol.*, 29:53–59 (1992); Jefferis et al., *Molec. Immunol.*, 27:1237–40 (1990); and Sarmay et al., *Molec. Immunol.*, 29:633–639 (1992).

Pro331 in IgG3 was changed to Ser, and the affinity of this mutant to target cells analyzed. The affinity was found to be six-fold lower than that of unmutated IgG3, indicating the involvement of Pro331 in FcγRI binding. Morrison et al., *Immunologist*, 2:119–124 (1994); and Canfield and Morrison, *J. Exp. Med.* 173:1483–91 (1991).

In addition, Glu318 was identified as being involved in binding to FcγRII. Ward and Ghetie, *Therapeutic Immunology* 2:77–94 (1995).

SUMMARY OF THE INVENTION

The present invention provides a variant of a polypeptide comprising a human IgG Fc region, which variant comprises an amino acid substitution at amino acid position 270 or 329, or at two or more of amino acid positions 270, 322, 329, and 331 of the human IgG Fc region, where the numbering of the residues in the IgG Fc region is that of the EU index as in Kabat.

The invention further relates to a variant of a polypeptide comprising a human IgG Fc region, which variant binds FcγRI, FcγRII, FcγRIII and FcRn but does not activate complement and comprises an amino acid substitution at amino acid position 322 or amino acid position 329, or both amino acid positions of the human IgG Fc region, where the numbering of the residues in the IgG Fc region is that of the EU index as in Kabat.

The invention also pertains to a variant of a parent polypeptide comprising a human IgG Fc region, which variant has a better binding affinity for human C1q than the parent polypeptide and comprises an amino acid substitution in the IgG Fc region. For example, the binding affinity of the variant for human C1q may be about two-fold or more improved compared to the binding affinity of the parent polypeptide for human C1q. Preferably the parent polypeptide binds C1q and mediates CDC (for example, the parent polypeptide may comprise a human IgG1, IgG2 or IgG3 Fc region). The variant with improved C1q binding preferably comprises an amino acid substitution at one or more of amino acid positions 326, 327, 333 and 334 of the human IgG Fc region, where the numbering of the residues in the IgG Fc region is that of the EU index as in Kabat.

In another aspect, the invention provides a variant of a polypeptide comprising a human IgG Fc region, which variant comprises an amino acid substitution at amino acid position 326, 327, 333 or 334 of the human IgG Fc region, where the numbering of the residues in the IgG Fc region is that of the EU index as in Kabat.

In yet a further aspect, the invention provides a method for modifying a polypeptide comprising a human IgG Fc region comprising substituting an amino acid residue at amino acid position 270 or 329, or at two or more of amino acid positions 270, 322, 329, and 331 of the human IgG Fc region, where the numbering of the residues in the IgG Fc region is that of the EU index as in Kabat.

The invention further provides a method for modifying a polypeptide comprising a human IgG Fc region comprising substituting an amino acid residue at amino acid position 326, 327, 333 or 334 of the human IgG Fc region, where the numbering of the residues in the IgG Fc region is that of the EU index as in Kabat. The method optionally further comprises a step wherein a variant with improved binding affinity for human C1q is identified.

The invention also provides a composition comprising the polypeptide variant and a physiologically acceptable carrier or diluent. This composition for potential therapeutic use is sterile and may be lyophilized.

Diagnostic and therapeutic uses for the polypeptide variant are contemplated. In one diagnostic application, the invention provides a method for determining the presence of a protein of interest comprising exposing a sample suspected of containing the protein to the polypeptide variant and determining binding of the polypeptide variant to the sample. In one therapeutic application, the invention provides a method of treating a mammal suffering from a disorder comprising administering to the mammal a therapeutically effective amount of a variant of a polypeptide comprising a human IgG Fc region, which variant binds FcγRI, FcγRII, FcγRIII and FcRn but does not activate complement and comprises an amino acid substitution at amino acid position 270, 322, 329 or 331 of the human IgG Fc region, where the numbering of the residues in the IgG Fc region is that of the EU index as in Kabat.

The invention further provides: isolated nucleic acid encoding the polypeptide variant; a vector comprising the nucleic acid, optionally, operably linked to control sequences recognized by a host cell transformed with the vector; a host cell comprising the vector; a process for producing the polypeptide variant comprising culturing this host cell so that the nucleic acid is expressed and, optionally, recovering the polypeptide variant from the host cell culture (e.g. from the host cell culture medium).

The invention also pertains to an immune complex comprising: (a) an Fc region-containing polypeptide; (b) a first target molecule which comprises at least two binding sites for the Fc region-containing polypeptide; and (c) a second target molecule comprises at least two binding sites for the first target molecule. The immune complex may be used in an FcR-binding assay, particularly where the FcR has a low affinity for the Fc region-containing polypeptide. Other uses for the immune complex are disclosed herein.

Moreover, the invention provides a method for determining binding of an analyte, such as an Fc region-containing polypeptide, to a receptor (e.g. a low affinity FcR) comprising the following steps performed sequentially: (a) forming a molecular complex between the analyte and a first target molecule, wherein the first target molecule comprises at least two binding sites for the analyte; and (b) determining binding of the molecular complex of step (a) to the receptor (e.g. to a binding domain of the receptor coated on an assay plate). Optionally, the molecular complex of step (a) further comprises a second target molecule which comprises at least two binding sites for the first target molecule.

The invention also relates to an assay kit, such as a kit useful for determining binding of an analyte to a receptor comprising: (a) a first target molecule which comprises at least two binding sites for the analyte; and (b) a second target molecule which comprises at least two binding sites for the first target molecule.

BRIEF DESCRIPTION OF THE DRAWINGS

FIGS. 4A (SEQ ID NO:1) and 4B (SEQ ID NO:2) depict the amino acid sequences of E27 anti-IgE antibody light chain (FIG. 4A) and heavy chain (FIG. 4B).

DETAILED DESCRIPTION OF PREFERRED EMBODIMENTS

I. Definitions

Throughout the present specification and claims, the numbering of the residues in an IgG heavy chain is that of the EU index as in Kabat et al., *Sequences of Proteins of Immunological Interest*, 5th Ed. Public Health Service, National Institutes of Health, Bethesda, Md. (1991), expressly incorporated herein by reference. The "EU index as in Kabat" refers to the residue numbering of the human IgG1 EU antibody.

Figure 1:
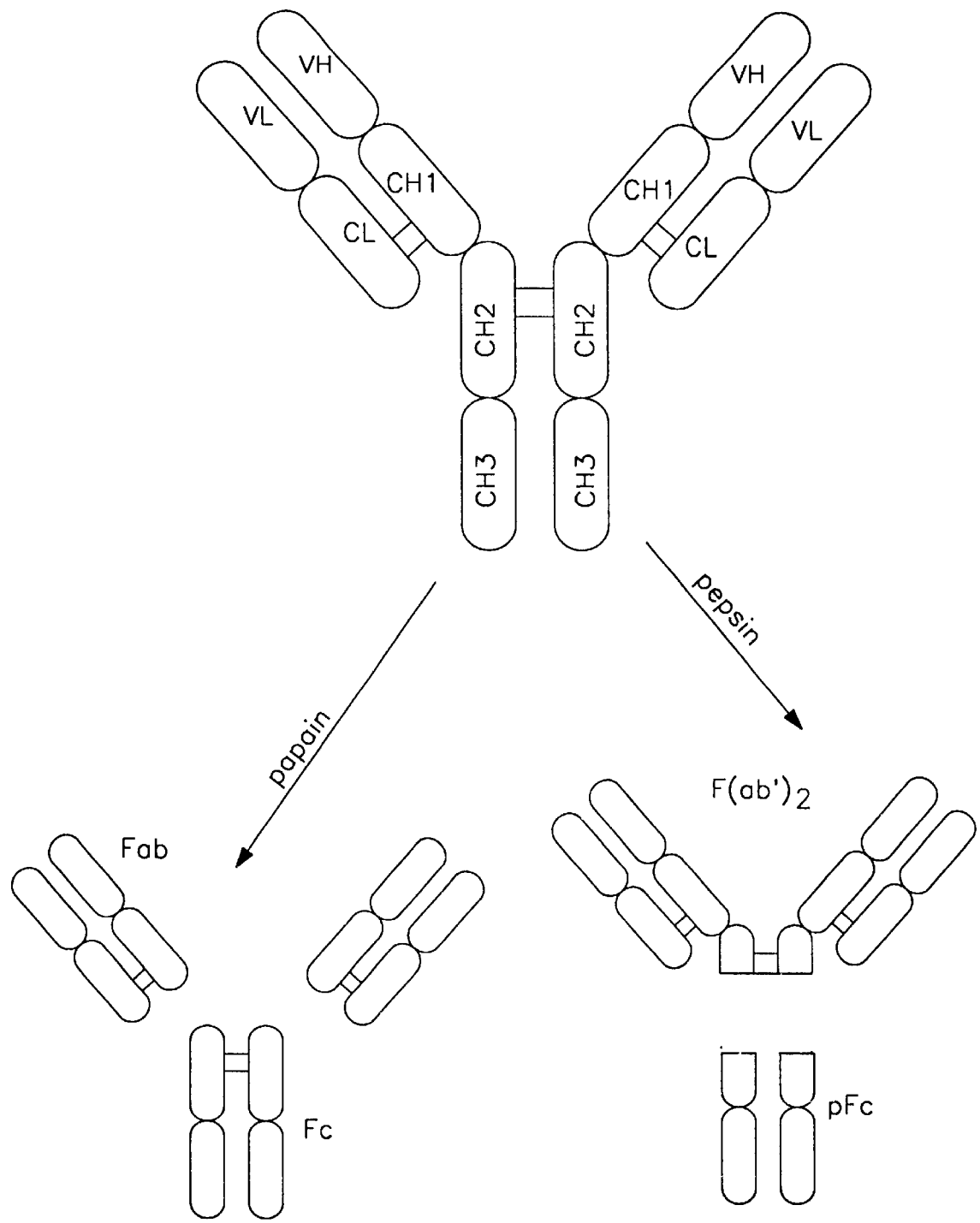
FIG. 1 is a schematic representation of a native IgG. Disulfide bonds are represented by heavy lines between CH1 and CL domains and the two CH2 domains. V is variable domain; C is constant domain; L stands for light chain and H stands for heavy chain.

The term "Fc region" is used to define a C-terminal region of an IgG heavy chain as shown in FIG. 1. Although the boundaries of the Fc region of an IgG heavy chain might vary slightly, the human IgG heavy chain Fc region is usually defined to stretch from amino acid residue at position Cys226 to the carboxyl-terminus. The term "Fc region-containing polypeptide" refers to a polypeptide, such as an antibody or immunoadhesin (see definitions below), which comprises an Fc region.

The Fc region of an IgG comprises two constant domains, CH2 and CH3, as shown in FIG. 1. The "CH2" domain of a human IgG Fc region (also referred to as "Cγ2" domain) usually extends from amino acid 231 to amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec. Immunol.* 22:161–206 (1985).

"Hinge region" is generally defined as stretching from Glu216 to Pro230 of human IgG1 (Burton, *Molec. Immunol.* 22:161–206 (1985)) Hinge regions of other IgG isotypes may be aligned with the IgG1 sequence by placing the first and last cysteine residues forming inter-heavy chain S—S bonds in the same positions.

"C1q" is a polypeptide that includes a binding site for the Fc region of an immunoglobulin. C1q together with two serine proteases, C1r and C1s, forms the complex C1, the first component of the complement dependent cytotoxicity (CDC) pathway. Human C1q can be purchased commercially from, e.g. Quidel, San Diego, Calif.

The term "Fc receptor" or "FcR" is used to describe a receptor that binds to the Fc region of an antibody. The preferred FcR is one, which binds an IgG antibody (a gamma receptor) and includes receptors of the FcγRI, FcγRII, and FcγRIII subclasses, including allelic variants and alternatively spliced forms of these receptors. FcRs are reviewed in Ravetch and Kinet, *Annu. Rev. Immunol* 9:457–92 (1991); Capel et al., *Immunomethods* 4:25–34 (1994); and de Haas et al., *J. Lab. Clin. Med.* 126:330–41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

The term "binding domain" refers to the region of a polypeptide that binds to another molecule. In the case of an FcR, the binding domain can comprise a portion of a polypeptide chain thereof (e.g. the α chain thereof which is responsible for binding an Fc region. One useful binding domain is the extracellular domain of an FcR α chain.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

"Antibody fragments", as defined for the purpose of the present invention, comprise a portion of an intact antibody, generally including the antigen binding or variable region of the intact antibody, so long as they retain at least the CH2 region of an IgG immunoglobulin heavy chain constant domain, comprising amino acid residues 322, 329 and 331, and have the ability, alone or in combination with another antibody fragment, to specifically bind a selected antigen. Examples of antibody fragments include linear antibodies; single-chain antibody molecules; and multispecific antibodies formed from antibody fragments. The antibody fragments preferably retain at least part of the hinge and optionally the CH1 region of an IgG heavy chain. More preferably, the antibody fragments retain the entire constant region of an IgG heavy chain, and include an IgG light chain.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624–628 (1991) and Marks et al., *J. Mol. Biol.* 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851–6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522–525 (1986); Riechmann et al., Nature 332:323–329 (1988); and Presta, Curr. Op. Struct. Biol. 2:593–596 (1992).

The term "hypervariable region" when used herein refers to the amino acid residues of an antibody which are responsible for antigen-binding. The hypervariable region comprises amino acid residues from a "complementarity determining region" or "CDR"(ie. residues 24–34 (L1), 50–56 (L2) and 89–97 (L3) in the light chain variable domain and 31–35 (H1), 50–65 (H2) and 95–102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop"(i.e. residues 26–32 (L1), 50–52 (L2) and 91–96 (L3) in the light chain variable domain and 26–32 (H1), 53–55 (H2) and 96–101 (H3) in the heavy chain variable domain; Chothia and Lesk J. Mol. Biol. 196:901–917 (1987)). "Framework" or "FR" residues are those variable domain residues other than the hypervariable region residues as herein defined.

As used herein, the term "immunoadhesin" designates antibody-like molecules which combine the "binding domain" of a heterologous "adhesin" protein (e.g. a receptor, ligand or enzyme) with an immunoglobulin constant domain. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence.

The term "ligand binding domain" as used herein refers to any native cell-surface receptor or any region or derivative thereof retaining at least a qualitative ligand binding ability of a corresponding native receptor. In a specific embodiment, the receptor is from a cell-surface polypeptide having an extracellular domain that is homologous to a member of the immunoglobulin supergenefamily. Other receptors, which are not members of the immunoglobulin supergenefamily but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules, e.g. (E-, L- and P-) selectins.

The term "receptor binding domain" is used to designate any native ligand for a receptor, including cell adhesion molecules, or any region or derivative of such native ligand retaining at least a qualitative receptor binding ability of a corresponding native ligand. This definition, among others, specifically includes binding sequences from ligands for the above-mentioned receptors.

An "antibody-immunoadhesin chimera" comprises a molecule that combines at least one binding domain of an antibody (as herein defined) with at least one immunoadhesin (as defined in this application). Exemplary antibody-immunoadhesin chimeras are the bispecific CD4-IgG chimeras described in Berg et al., PNAS (USA) 88:4723–4727 (1991) and Chamow et al., J. Immunol. 153:4268 (1994).

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

"Treatment" refers to both therapeutic treatment and prophylactic or preventative measures. Those in need of treatment include those already with the disorder as well as those in which the disorder is to be prevented.

A "disorder" is any condition that would benefit from treatment with the polypeptide variant. This includes chronic and acute disorders or diseases including those pathological conditions which predispose the mammal to the disorder in question.

The word "label" when used herein refers to a detectable compound or composition which is conjugated directly or indirectly to the polypeptide. The label may be itself be detectable (e.g., radioisotope labels or fluorescent labels) or, in the case of an enzymatic label, may catalyze chemical alteration of a substrate compound or composition which is detectable.

An "isolated" nucleic acid molecule is a nucleic acid molecule that is identified and separated from at least one contaminant nucleic acid molecule with which it is ordinarily associated in the natural source of the polypeptide nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the polypeptide where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "molecular complex" when used herein refers to the relatively stable structure which forms when two or more heterologous molecules (e.g. polypeptides) bind (preferably noncovalently) to one another. The preferred molecular complex herein is an immune complex.

"Immune complex" refers to the relatively stable structure which forms when at least one target molecule and at least one heterologous Fc region-containing polypeptide bind to one another forming a larger molecular weight complex. Examples of immune complexes are antigen-antibody aggregates and target molecule-immunoadhesin aggregates. The term "immune complex" as used herein, unless indicated otherwise, refers to an ex vivo complex (i.e. other than the form or setting in which it may be found in nature). However, the immune complex may be administered to a mammal, e.g. to evaluate clearance of the immune complex in the mammal.

The term "target molecule" refers to a molecule, usually a polypeptide, which is capable of being bound by a heterologous molecule and has one or more binding sites for the heterologous molecule. The term "binding site" refers to a region of a molecule to which another molecule can bind. The "first target molecule" herein comprises at least two distinct binding sites (for example, two to five separate binding sites) for an analyte (e.g. an Fc region-containing polypeptide) such that at least two analyte molecules can bind to the first target molecule. In the preferred embodiment of the invention, the two or more binding sites are identical (e.g. having the same amino acid sequence, where the target molecule is a polypeptide). In Example 1 below, the first target molecule was IgE and had two separate binding sites in the Fc region thereof to which the Fc region-containing polypeptide (an anti-IgE antibody, E27) could bind. Other first target molecules include dimers of substantially identical monomors (e.g. neurotrophins, IL8 and VEGF) or are polypeptides comprising two or more substantially identical polypeptide chains (e.g. antibodies or immunoadhesins). The "second target molecule" comprises at least two distinct binding sites (for example, two to five separate binding sites) for the first target molecule such that at least two first target molecules can bind to the second target molecule. Preferably, the two or more binding sites are identical (e.g. having the same amino acid sequence, where the target molecule is a polypeptide). In Example 2, the second target molecule was VEGF, which has a pair of distinct binding sites to which the variable domain of the IgE antibody could bind. Other second target molecules are contemplated, e.g. other dimers of substantially identical monomers (e.g. neurotrophins or IL8) or polypeptides comprising two or more substantially identical domains (e.g. antibodies or immunoadhesins).

An "analyte" is a substance that is to be analyzed. The preferred analyte is an Fc region-containing polypeptide that is to be analyzed for its ability to bind to an Fc receptor.

A "receptor" is a polypeptide capable of binding at least one ligand. The preferred receptor is a cell-surface receptor having an extracellular ligand-binding domain and, optionally, other domains (e.g. transmembrane domain, intracellular domain and/or membrane anchor). The receptor to be evaluated in the assay described herein may be an intact receptor or a fragment or derivative thereof (e.g. a fusion protein comprising the binding domain of the receptor fused to one or more heterologous polypeptides). Moreover, the receptor to be evaluated for its binding properties may be present in a cell or isolated and optionally coated on an assay plate or some other solid phase.

The phrase "low affinity receptor" denotes a receptor that has a weak binding affinity for a ligand of interest, e.g. having a binding constant of about 50 nM or worse affinity. Exemplary low affinity receptors include FcγRII and FcγRIII as well as adhesion molecules, such as integrins.

A "parent polypeptide" is a polypeptide comprising an amino acid sequence which lacks one or more of the Fc region substitutions disclosed herein and/or which differs in effector function compared to a polypeptide variant as herein disclosed. The parent polypeptide may comprise a native sequence Fc region or an Fc region with existing amino acid sequence modifications (such as additions, deletions and/or substitutions).

II. Modes for Carrying Out the Invention

The invention herein relates to a method for making a polypeptide variant. The "parent", "starting" or "nonvariant" polypeptide is prepared using techniques available in the art for generating polypeptides comprising an Fc region. In the preferred embodiment of the invention, the polypeptide is an antibody and exemplary methods for generating antibodies are described in more detail in the following sections. The polypeptide may, however, be any other polypeptide comprising an Fc region, e.g. an immunoadhesin. Methods for making immunoadhesins are elaborated in more detail hereinbelow.

The starting polypeptide of particular interest herein is usually one that binds to C1q and displays complement dependent cytotoxicity (CDC). The amino acid substitutions described herein will generally serve to alter the ability of the starting polypeptide to bind to C1q and/or modify its complement dependent cytotoxicity function, e.g. to reduce and preferably abolish these effector functions. However, polypeptides comprising substitutions at one or more of the described positions with improved effector functions are contemplated herein. For example, the starting polypeptide may be unable to bind C1q and/or mediate CDC and may be modified according to the teachings herein such that it acquires these effector functions. Moreover, polypeptides with pre-existing C1q binding activity, optionally further having the ability to mediate CDC may be modified such that one or both of these activities are enhanced.

To generate the polypeptide variant, one or more amino acid alterations (e.g. substitutions) are introduced in the Fc region of the starting polypeptide. The amino acid positions to be modified are generally selected from heavy chain positions 270, 322, 326, 327, 329, 331, 333, and 334, where the numbering of the residues in an IgG heavy chain is that of the EU index as in Kabat et al., *Sequences of Proteins of Immunological Interest*, 5th Ed. Public Health Service, National Institutes of Health, Bethesda, Md. (1991). The Fc region is preferably from a human IgG and most preferably a human IgG1 or human IgG3. The human IgG1 Fc region may be a human A or non-A allotype.

Proline is conserved at position 329 in human IgG's. This residue is preferably replaced with alanine, however substitution with any other amino acid is contemplated, e.g., serine, threonine, asparagine, glycine or valine.

Proline is conserved at position 331 in human IgG1, IgG2 and IgG3, but not IgG4 (which has a serine residue at position 331). Residue 331 is preferably replaced by alanine or another amino acid, e.g. serine (for IgG regions other than IgG4), glycine or valine.

Lysine 322 is conserved in human IgGs, and this residue is preferably replaced by an alanine residue, but substitution with any other amino acid residue is contemplated, e.g. serine, threonine, glycine or valine.

D270 is conserved in human IgGs, and this residue may be replaced by another amino acid residue, e.g. alanine, serine, threonine, glycine, valine, or lysine.

K326 is also conserved in human IgGs. This residue may be substituted with another residue including, but not limited to, valine, glutamic acid, alanine, glycine, aspartic acid, methionine or tryptophan, with tryptophan being preferred.

Likewise, E333 is also conserved in human IgGs. E333 is preferably replaced by an amino acid residue with a smaller side chain volume, such as valine, glycine, alanine or serine, with serine being preferred.

K334 is conserved in human IgGs and may be substituted with another residue such as alanine or other residue.

In human IgG1 and IgG3, residue 327 is an alanine. In order to generate a variant with improved C1q binding, this alanine may be substituted with another residue such as glycine. In IgG2 and IgG4, residue 327 is a glycine and this may be replaced by alanine (or another residue) to diminish C1q binding.

Preferably, substitutions at two, three or all of positions 326, 327, 333 or 334 are combined, optionally with other Fc region substitutions, to generate a polypeptide with improved human C1q binding and preferably improved CDC activity in vitro or in vivo.

In one embodiment, only one of the eight above-identified positions is altered in order to generate the polypeptide variant. Preferably only residue 270, 329 or 322 is altered if this is the case. Alternatively, two or more of the above-identified positions are modified. If substitutions are to be combined, generally substitutions which enhance human C1q binding (e.g. at residue positions 326, 327, 333 and 334) or those which diminish human C1q binding (e.g., at residue positions 270, 322, 329 and 331) are combined. In the latter embodiment, all four positions (ie., 270, 322, 329 and 331) may be substituted. A variant may be generated in which the native amino acid residue at position 329 of the human heavy chain constant region is substituted with another amino acid, optionally in combination with a substitution of the amino acid residue at position 331 and/or substitution of the amino acid residue at position 322. Otherwise, the native amino acid residue at position 331 and the native amino acid residue at position 322 of the human IgG Fc region may both be substituted with another amino acid residue. One may also combine an amino acid substitution at position 270 with further substitution(s) at position(s) 322, 329 and/or 331.

DNA encoding amino acid sequence variant of the starting polypeptide is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide Site-directed mutagenesis is a preferred method for preparing substitution variants. This technique is well known in the art (see, e.g.,Carter et al. *Nucleic Acids Res.* 13:4431–4443 (1985) and Kunkel et al., *Proc. Natl. Acad.Sci.USA* 82:488 (1987)). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the starting polypeptide. See Higuchi, in *PCR Protocols*, pp.177–183 (Academic Press, 1990); and Vallette et al., *Nuc. Acids Res.* 17:723–733 (1989). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., *Gene* 34:315–323 (1985). The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence encoding a polypeptide variant can be determined, and a nucleic acid sequence encoding such amino acid sequence variant can be generated synthetically.

The polypeptide variant(s) so prepared may be subjected to further modifications, oftentimes depending on the intended use of the polypeptide. Such modifications may involve further alteration of the amino acid sequence, fusion to heterologous polypeptide(s) and/or covalent modifications.

For example, it may be useful to combine the above amino acid substitutions with one or more further amino acid substitutions that reduce or ablate FcR binding. For example, the native amino acid residues at any one or more of heavy chain positions 233–238, 318 or 331 (where the numbering of the residues in an IgG heavy chain is that of the EU index as in Kabat et al., supra) may be replaced with non-native residue(s), e.g. alanine.

With respect to further amino acid sequence alterations, any cysteine residue not involved in maintaining the proper conformation of the polypeptide variant also may be substituted, generally with serine, to improve the oxidative stability of the molecule and prevent aberrant cross linking.

Another type of amino acid substitution serves to alter the glycosylation pattern of the polypeptide. This may be achieved by deleting one or more carbohydrate moieties found in the polypeptide, and/or adding one or more glycosylation sites that are not present in the polypeptide. Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original polypeptide (for O-linked glycosylation sites). An exemplary glycosylation variant has an amino acid substitution of residue Asn 297 of the heavy chain.

The polypeptide variant may be subjected to one or more assays to evaluate any change in biological activity compared to the starting polypeptide. For example, the ability of the variant to bind C1q and mediate complement dependent cytotoxicity (CDC) may be assessed.

To determine C1q binding, a C1q binding ELISA may be performed. Briefly, assay plates may be coated overnight at 4° C. with polypeptide variant or starting polypeptide (control) in coating buffer. The plates may then be washed and blocked. Following washing, an aliquot of human C1q may be added to each well and incubated for 2 hrs at room temperature. Following a further wash, 100 µl of a sheep anti-complement C1q peroxidase conjugated antibody may be added to each well and incubated for 1 hour at room temperature. The plate may again be washed with wash buffer and 100 µl of substrate buffer containing OPD (O-phenylenediamine dihydrochloride (Sigma)) may be added to each well. The oxidation reaction, observed by the appearance of a yellow color, may be allowed to proceed for 30 minutes and stopped by the addition of 100 µl of 4.5 N $H_2SO_4$. The absorbance may then read at (492–405) nm.

An exemplary polypeptide variant is one that displays a "significant reduction in C1q binding" in this assay. This means that about 100 µg/ml of the polypeptide variant displays about 50 fold or more reduction in C1q binding compared to 100 µg/ml of a control antibody having a nonmutated IgG1 Fc region. In the most preferred embodiment, the polypeptide variant "does not bind C1q", ie. 100 µg/ml of the polypeptide variant displays about 100 fold or more reduction in C1q binding compared to 100 µg/ml of the control antibody.

Another exemplary variant is one which "has a better binding affinity for human C1q than the parent polypeptide". Such a molecule may display, for example, about two-fold or more, and preferably about five-fold or more, improvement in human C1q binding compared to the parent polypeptide (e.g. at the $IC_{50}$ values for these two molecules). For example, human C1q binding may be about two-fold to about 500-fold, and preferably from about two-fold or from about five-fold to about 1000-fold improved compared to the parent polypeptide.

To assess complement activation, a complement dependent cytotoxicity (CDC) assay may be performed, e.g. as described in Gazzano-Santoro et al., *J. Immunol. Methods* 202:163 (1996). Briefly, various concentrations of the polypeptide variant and human complement may be diluted with buffer. Cells which express the antigen to which the polypeptide variant binds may be diluted to a density of ~1×10⁶ cells /ml. Mixtures of polypeptide variant, diluted human complement and cells expressing the antigen may be added to a flat bottom tissue culture 96 well plate and allowed to incubate for 2 hrs at 37° C. and 5% $CO_2$ to facilitate complement mediated cell lysis. 50 µl of alamar blue (Accumed International) may then be added to each well and incubated overnight at 37° C. The absorbance is measured using a 96-well fluorometer with excitation at 530 nm and emission at 590 nm. The results may be expressed in relative fluorescence units (RFU). The sample concentrations may be computed from a standard curve and the percent activity as compared to nonvariant polypeptide is reported for the polypeptide variant of interest.

Yet another exemplary variant "does not activate complement". For example, 0.6 µg/ml of the polypeptide variant displays about 0–10% CDC activity in this assay compared to a 0.6 µg/ml of a control antibody having a nonmutated IgG1 Fc region. Preferably the variant does not appear to have any CDC activity in the above CDC assay.

The invention also pertains to a polypeptide variant with enhanced CDC compared to a parent polypeptide, e.g., displaying about two-fold to about 100-fold improvement in CDC activity in vitro or in vivo (e.g. at the $IC_{50}$ values for each molecule being compared).

Preferably the polypeptide variant essentially retains the ability to bind antigen compared to the nonvariant polypeptide, ie. the binding capability is no worse than about 20 fold, e.g. no worse than about 5 fold of that of the nonvariant polypeptide. The binding capability of the polypeptide variant may be determined using techniques such as fluorescence activated cell sorting (FACS) analysis or radioimmunoprecipitation (RIA), for example.

The ability of the polypeptide variant to bind an FcR may also be evaluated. Where the FcR is a high affinity Fc receptor, such as FcγRI or FcRn, binding can be measured by titrating monomeric polypeptide variant and measuring bound polypeptide variant using an antibody which specifically binds to the polypeptide variant in a standard ELISA format (see Example 2 below). Another FcR binding assay for low affinity FcRs is elaborated in more detail in the following section.

Preferably the variant retains the ability to bind one or more FcRs, e.g. the ability of the polypeptide variant to bind FcγRI, FcγRII, FcγRIII and/or FcRn is no more than about 20 fold reduced, preferably no more than about 10 fold reduced, and most preferably no more than about two fold reduced compared to the starting polypeptide as determined in the FcγRI or FcRn assays of Example 2 or the FcγRII or FcγRIII assays described in the following section.

A. Receptor Binding Assay and Immune Complex

A receptor binding assay has been developed herein which is particularly useful for determining binding of an analyte of interest to a receptor where the affinity of the analyte for the receptor is relatively weak, e.g. in the micromolar range as is the case for FcγRIIa, FeγRIIb, FcγRIIIa and FcγRIIIb. The method involves the formation of a molecular complex that has an improved avidity for the receptor of interest compared to the noncomplexed analyte. The preferred molecular complex is an immune complex comprising: (a) an Fc region-containing polypeptide (such as an antibody or an immunoadhesin); (b) a first target molecule which comprises at least two binding sites for the Fc region-containing polypeptide; and (c) a second target molecule which comprises at least two binding sites for the first target molecule.

Figure 5:
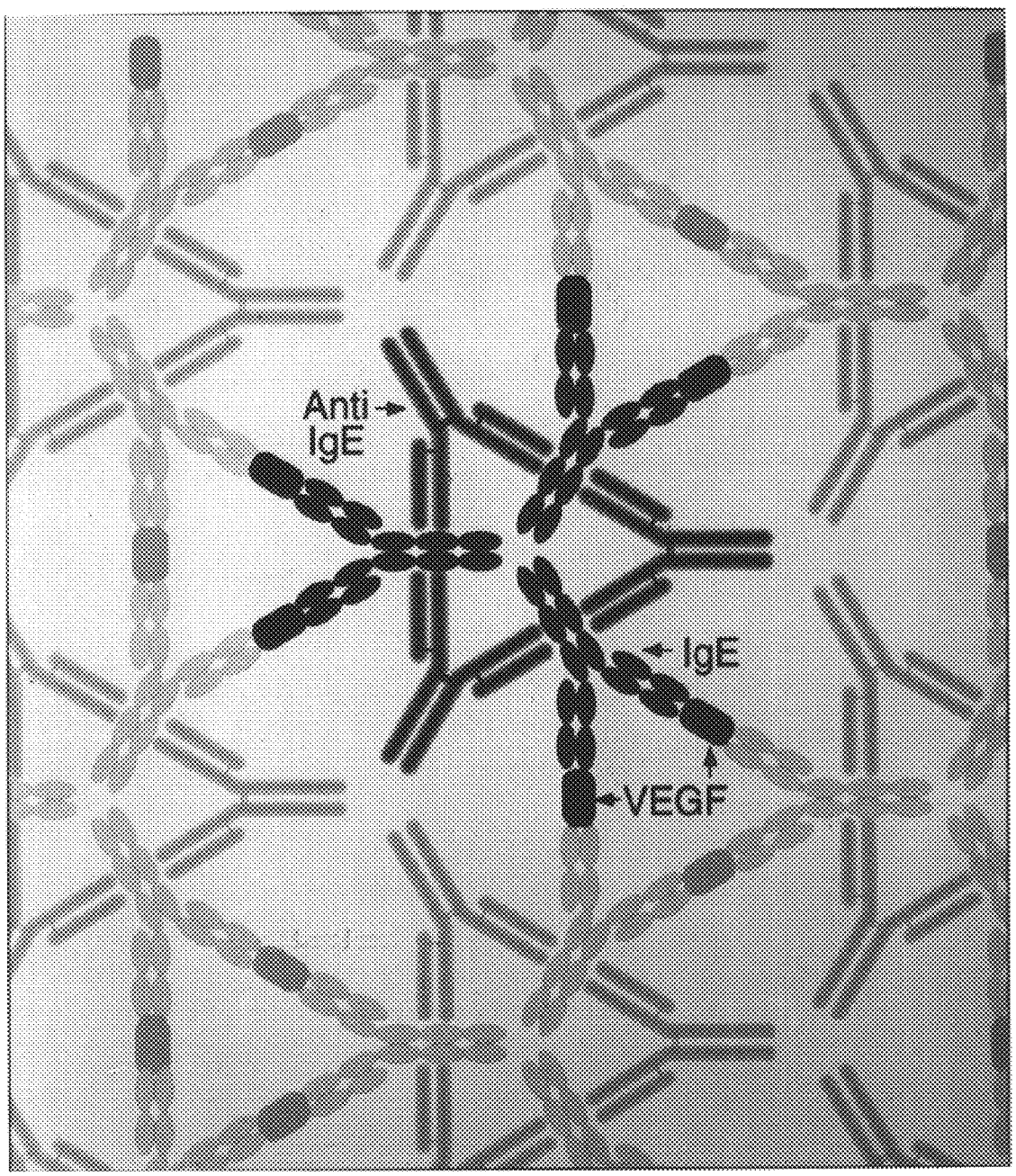
FIG. 5 is a schematic diagram of the "immune complex" prepared for use in the FcR assay described in Example 1. The hexamer comprising three anti-IgE antibody molecules (the "Fc region-containing polypeptide") and three IgE molecules (the "first target molecule") is shown. IgE has two "binding sites" for the anti-IgE antibody (E27) in the Fc region thereof. Each IgE molecule in the complex is further able to bind two VEGF molecules ("the second target polypeptide"). VEGF has two "binding sites" for IgE.

In Example 1 below, the Fc region-containing polypeptide is an anti-IgE antibody, such as the E27 antibody (FIGS. 4A–4B). E27, when mixed with human IgE at an 1:1 molar ratio, forms a stable hexamer consisting of three E27 molecules and three IgE molecules. In Example 1 below, the "first target molecule" is a chimeric form of IgE in which the Fab portion of an anti-VEGF antibody is fused to the human IgE Fc portion and the "second target molecule" is the antigen to which the Fab binds (ie. VEGF). Each molecule of IgE binds two molecules of VEGF. VEGF also binds two molecules of IgE per molecule of VEGF. When recombinant human VEGF was added at a 2:1 molar ratio to IgE:E27 hexamers, the hexamers were linked into larger molecular weight complexes via the IgE:VEGF interaction (FIG. 5). The Fc region of the anti-IgE antibody of the resultant immune complex binds to FcR with higher avidity than either uncomplexed anti-IgE or anti-IgE:IgE hexamers.

Other forms of molecular complexes for use in the receptor assay are contemplated. Examples comprising only an Fc region-containing polypeptide:first target molecule combination include an immunoadhesin:ligand combination such as VEGF receptor (KDR)-immunoadhesin:VEGF and a full-length bispecific antibody (bsAb):first target molecule. A further example of an Fc region-containing polypeptide-:first target molecule:second target molecule combination include a nonblocking antibody:soluble receptor:ligand combination such as anti-Trk antibody:soluble Trk receptor:neurotrophin (Urfer et al. *J. Biol. Chem.* 273(10) :5829–5840 (1998)).

Aside from use in a receptor binding assay, the immune complexes described above have further uses including evaluation of Fc region-containing polypeptide function and immune complex clearance in vivo. Hence, the immune complex may be administered to a mammal (e.g. in a pre-clinical animal study) and evaluated for its half-life etc.

To determine receptor binding, a polypeptide comprising at least the binding domain of the receptor of interest (e.g. the extracellular domain of an α subunit of an FcR) may be coated on solid phase, such as an assay plate. The binding domain of the receptor alone or a receptor-fusion protein may be coated on the plate using standard procedures. Examples of receptor-fusion proteins include receptor-glutathione S-transferase (GST) fusion protein, receptor-chitin binding domain fusion protein, receptor-hexaHis tag fusion protein (coated on glutathione, chitin, and nickel coated plates, respectively). Alternatively, a capture molecule may be coated on the assay plate and used to bind the receptor-fusion protein via the non-receptor portion of the fusion protein. Examples include anti-hexaHis F(ab')$_2$ coated on the assay plate used to capture receptor-hexaHis tail fusion or anti-GST antibody coated on the assay plate used to capture a receptor-GST fusion. In other embodiments, binding to cells expressing at least the binding domain of the receptor may be evaluated. The cells may be naturally occurring hematopoietic cells that express the FcR of interest or may be transformed with nucleic acid encoding the FcR or a binding domain thereof such that the binding domain is expressed at the surface of the cell to be tested.

The immune complex described hereinabove is added to the receptor-coated plates and incubated for a sufficient period of time such that the analyte binds to the receptor. Plates may then be washed to remove unbound complexes, and binding of the analyte may be detected according to known methods. For example, binding may be detected using a reagent (e.g. an antibody or fragment thereof) which binds specifically to the analyte, and which is optionally conjugated with a detectable label (detectable labels and methods for conjugating them to polypeptides are described below in the section entitled "Non-Therapeutic Uses for the Polypeptide Variant").

As a matter of convenience, the reagents can be provided in an assay kit, i.e., a packaged combination of reagents, for combination with the analyte in assaying the ability of the analyte to bind to a receptor of interest. The components of the kit will generally be provided in predetermined ratios. The kit may provide the first target molecule and/or the second target molecule, optionally complexed together. The kit may further include assay plates coated with the receptor or a binding domain thereof (e.g. the extracellular domain of the a subunit of an FcR). Usually, other reagents, such as an antibody that binds specifically to the analyte to be assayed, labeled directly or indirectly with an enzymatic label, will also be provided in the kit. Where the detectable label is an enzyme, the kit will include substrates and cofactors required by the enzyme (e.g. a substrate precursor which provides the detectable chromophore or fluorophore). In addition, other additives may be included such as stabilizers, buffers (e.g. assay and/or wash lysis buffer) and the like. The relative amounts of the various reagents may be varied widely to provide for concentrations in solution of the reagents that substantially optimize the sensitivity of the assay. Particularly, the reagents may be provided as dry powders, usually lyophilized, including excipients that on dissolution will provide a reagent solution having the appropriate concentration. The kit also suitably includes instructions for carrying out the assay.

B. Antibody Preparation

In the preferred embodiment of the invention, the Fc region-containing polypeptide which is modified according to the teachings herein is an antibody. Techniques for producing antibodies follow:

(i) Antigen selection and preparation

Where the polypeptide is an antibody, it is directed against an antigen of interest. Preferably, the antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated.

Where the antigen is a polypeptide, it may be a transmembrane molecule (e.g. receptor) or ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clofting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-$\beta$; platelet-derived growth factor (PDGF); fibroblast growth factor such as aFGF and bFGF; epidermal growth factor (EGF); transforming growth factor (TGF) such as TGF-alpha and TGF-beta, including TGF-$\beta$1, TGF-$\beta$2, TGF-$\beta$3, TGF-$\beta$4, or TGF-$\beta$5; insulin-like growth factor-I and -II (IGF-I and IGF-II); des(1–3)-IGF-I (brain IGF-I), insulin-like growth factor binding proteins; CD proteins such as CD3, CD4, CD8, CD1 9 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11 a, CD11 b, CD11 c, CD18, an ICAM, VLA-4 and VCAM; a tumor associated antigen such as HER2, HER3 or HER4 receptor; and fragments of any of the above-listed polypeptides.

Preferred molecular targets for antibodies encompassed by the present invention include CD proteins such as CD3, CD4, CD8, CD19, CD20 and CD34; members of the ErbB receptor family such as the EGF receptor, HER2, HER3 or HER4 receptor; cell adhesion molecules such as LFA-1, Mac1, p150.95, VLA-4, ICAM-1, VCAM and $\alpha v/\beta 3$ integrin including either $\alpha$ or $\beta$ subunits thereof (e.g. anti-CD11 a, anti-CD18 or anti-CD11 b antibodies); growth factors such as VEGF; IgE; blood group antigens; flk2/flt3 receptor; obesity (OB) receptor; mpl receptor; CTLA-4; protein C etc.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

(ii) Polyclonal antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 $\mu$g or 5 $\mu$g of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp.59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Pro-* duction Techniques and Applications, pp. 51–63 (Marcel Dekker, Inc., New York,1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp.59–103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described in McCafferty et al., *Nature*, 348:552–554 (1990). Clackson et al., *Nature*, 352:624–628 (1991) and Marks et al., *J. Mol. Biol.*, 222:581–597 (1991) describe the isolation of murine and human antibodies, respectively, using phage libraries. Subsequent publications describe the production of high affinity (nM range) human antibodies by chain shuffling (Marks et al., *Bio/Technology*, 10:779–783 (1992)), as well as combinatorial infection and in vivo recombination as a strategy for constructing very large phage libraries (Waterhouse et al., *Nuc. Acids. Res.*, 21:2265–2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iv) Humanized and human antibodies

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immnol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255–258 (1993); Bruggermann et al., *Year in Immuno.*, 7:33 (1993); and Duchosal et al. *Nature* 355:258 (1992). Human antibodies can also be derived from phage-display libraries (Hoogenboom et al.,*J. Mol. Biol.*, 227:381 (1991); Marks et al., *J. Mol. Biol.*, 222:581–597 (1991); Vaughan et al. *Nature Biotech* 14:309 (1996)).

(v) Multispecific antibodies

Multispecific antibodies have binding specificities for at least two different antigens. While such molecules normally will only bind two antigens (i.e. bispecific antibodies, BsAbs), antibodies with additional specificities such as trispecific antibodies are encompassed by this expression when used herein. Examples of BsAbs include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell ahesion molecule (NCAM)/anti-CD3, anti-folate binding protein (FBP)/anti-CD3, anti-pan carcinoma associated antigen (AMOC-31 )/anti-CD3; BsAbs with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α (IFN-a)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tissue plasminogen activator (tPA), anti-fibrin/anti-urokinase-type plasminogen activator (uPA); BsAbs for targeting immune complexes to cell surface receptors such as anti-low density lipoprotein (LDL)/anti-Fc receptor (e.g. FcγRI, FcγRII or FcγRIII); BsAbs for use in therapy of infectious diseases such as anti-CD3/anti-herpes simplex virus (HSV), anti-T-cell receptor:CD3 complex/anti-influenza, anti-FcγR/anti-HIV; BsAbs for tumor detection in vitro or in vivo such as anti-CEA/anti-EOTUBE, anti-CEA/anti-DPTA, anti-p185$^{HER2}$/anti-hapten; BsAbs as vaccine adjuvants; and BsAbs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase. Examples of trispecific antibodies include anti-CD3/anti-CD4/anti-CD37, anti-CD3/anti-CD5/anti-CD37 and anti-CD3/anti-CD8/anti-CD37. Bispecific antibodies can be prepared as full length antibodies or antibody fragments (e.g. F(ab')$_2$bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655–3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Antibodies with more than two valencies are contemplated. For example, trispecific antibodies can be prepared. Tutt et al. *J. Immunol.* 147: 60 (1991).

While the polypeptide of interest herein is preferably an antibody, other Fc region-containing polypeptides which can be modified according to the methods described herein are contemplated. An example of such a molecule is an immunoadhesin.

C. Immunoadhesin Preparation

The simplest and most straightforward immunoadhesin design combines the binding domain(s) of the adhesin (e.g. the extracellular domain (ECD) of a receptor) with the Fc region of an immunoglobulin heavy chain. Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain, or immediately N-terminal to the $C_H1$ of the heavy chain or the corresponding region of the light chain. The precise site at which the fusion is made is not critical; particular sites are well known and may be selected in order to optimize the biological activity, secretion, or binding characteristics of the immunoadhesin.

In a preferred embodiment, the adhesin sequence is fused to the N-terminus of the Fc region of immunoglobulin $G_1$ ($IgG_1$). It is possible to fuse the entire heavy chain constant region to the adhesin sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the adhesin amino acid sequence is fused to (a) the hinge region and $C_H2$ and $C_H3$ or (b) the $C_H1$, hinge, $C_H2$ and $C_H3$ domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which igG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled immunoadhesins within the scope herein are schematically diagrammed below:

(a) $AC_L$-$AC_L$;
(b) $AC_H$-($AC_H$, $AC_L$-$AC_H$, $AC_L$-$VHC_H$, or $V_LC_L$-$AC_H$);
(c) $AC_L$-$AC_H$-($AC_L$-$AC_H$, $AC_L$-$V_HC_H$, $V_LC_L$-$AC_H$, or $V_LC_L$-$V_HC_H$)
(d) $AC_L$-$V_HC_H$-($AC_H$, or $AC_L$-$V_HC_H$, or $V_LC_L$-$AC_H$);
(e) $V_LC_L$-$AC_H$-($AC_L$-$V_HC_H$, or $V_LC_L$-$AC_H$); and
(f) $(A-Y)_n$-$(V_LC_L$-$V_HC_H)_2$, wherein each A represents identical or different adhesin amino acid sequences;

$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $C_H2$ domain, or between the $C_H2$ and $C_H3$ domains. Similar constructs have been reported by Hoogenboom, et a., *Mol. Immunol.* 28:1027–1037 (1991).

Although the presence of an immunoglobulin light chain is not required in the immunoadhesins of the present invention, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued Mar. 28, 1989.

Immunoadhesins are most conveniently constructed by fusing the cDNA sequence encoding the adhesin portion in-frame to an immunoglobulin cDNA sequence. However, fusion to genomic immunoglobulin fragments can also be used (see, e.g. Aruffo et al., *Cell* 61 :1303–1313 (1990); and Stamenkovic et al., Cell 66:1133–1144 (1991)). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin are inserted in tandem into a plasmid vector that directs efficient expression in the chosen host cells.

D. Vectors, Host Cells and Recombinant Methods

The invention also provides isolated nucleic acid encoding a polypeptide variant as disclosed herein, vectors and host cells comprising the nucleic acid, and recombinant techniques for the production of the polypeptide variant.

For recombinant production of the polypeptide variant, the nucleic acid encoding it is isolated and inserted into a replicable vector for further cloning (amplification of the DNA) or for expression. DNA encoding the polypeptide variant is readily isolated and sequenced using conventional procedures (e.g., by using oligonucleotide probes that are capable of binding specifically to genes encoding the polypeptide variant). Many vectors are available. The vector components generally include, but are not limited to, one or more of the following: a signal sequence, an origin of replication, one or more marker genes, an enhancer element, a promoter, and a transcription termination sequence.

(i) Signal sequence component

The polypeptide variant of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native polypeptide variant signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, α factor leader (including Saccharomyces and Kluyveromyces α-factor leaders), or acid phosphatase leader, the C. albicans glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the polypeptide variant.

(ii) Origin of replication component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 $\mu$ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection gene component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the polypeptide variant nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding polypeptide variant, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 $\mu$m circular plasmid pKD1 can be used for transformation of Kluyveromyces yeasts. Alternatively, an expression system for large-scale production of recombinant calf chymosin was reported for K. lactis. Van den Berg, Bio/Technology, 8:135 (1990). Stable multi-copy expression vectors for secretion of mature recombinant human serum albumin by industrial strains of Kluyveromyces have also been disclosed. Fleer et al., Bio/Technology, 9:968–975 (1991).

(iv) Promoter component

Expression and cloning vectors usually contain a promoter that is recognized by the host organism and is operably linked to the polypeptide variant nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the polypeptide variant.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Polypeptide variant transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a Hindlil E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598–601 (1982) on expression of human β-interferon cDNA in mouse cells under the control of a thymidine kinase promoter from herpes simplex virus. Alternatively, the rous sarcoma virus long terminal repeat can be used as the promoter.

(v) Enhancer element component

Transcription of a DNA encoding the polypeptide variant of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature* 297:17–18 (1982) on enhancing elements for activation of eukaryotic promoters. The enhancer may be spliced into the vector at a position 5' or 3' to the polypeptide variant-encoding sequence, but is preferably located at a site 5' from the promoter.

(vi) Transcription termination component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide variant. One useful transcription termination component is the bovine growth hormone polyadenylation region. See WO94/11026 and the expression vector disclosed therein.

(vii) Selection and transformation of host cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as Escherichia, e.g., *E coli*, Enterobacter, Erwinia, Klebsiella, Proteus, Salmonella, e.g., *Salmonella typhimurium*, Serratia, e.g., *Serratia marcescans*, and Shigella, as well as Bacilli such as *B. subtilis* and *B. licheniformis* (e.g., *B. licheniformis* 41P disclosed in DD 266,710 published Apr. 12, 1989), Pseudomonas such as *P. aeruginosa*, and Streptomyces. One preferred *E. coli* cloning host is *E. coil* 294 (ATCC 31,446), although other strains such as *E. coli* B, *E. coli* X1776 (ATCC 31,537), and *E coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide variant-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; Kluyveromyces hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; yarrowia (EP 402,226); *Pichia pastoris* (EP 183,070); Candida; *Trichoderma reesia* (EP 244,234); Neurospora crassa; Schwanniomyces such as *Schwanniomyces occidentals*; and filamentous fungi such as, e.g., Neurospora, Penicillium, Tolypocladium, and Aspergillus hosts such as *A. nidulans* and *A. niger*.

Suitable host cells for the expression of glycosylated polypeptide variant are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster*(fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44–68 (1982)); MRC 5 cells; FS4 cells; and a human hepatoma line (Hep G2).

Host cells are transformed with the above-described expression or cloning vectors for polypeptide variant production and cultured in conventional nutrient media modified as appropriate for inducing promoters, selecting transformants, or amplifying the genes encoding the desired sequences.

(viii) Culturing the host cells

The host cells used to produce the polypeptide variant of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem*.102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMY-CIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Polypeptide variant purification

When using recombinant techniques, the polypeptide variant can be produced intracellularly, in the periplasmic space, or directly secreted into the medium. If the polypeptide variant is produced intracellularly, as a first step, the particulate debris, either host cells or lysed fragments, is removed, for example, by centrifugation or ultrafiltration. Carter et al., *Bio/Technology* 10:163–167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the polypeptide variant is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The polypeptide variant composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc region that is present in the polypeptide variant. Protein A can be used to purify polypeptide variants that are based on human γ1, γ2, or γ4 heavy chains (Lindmark et al., *J. Immunol. Meth.* 62:1–13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly (styrenedivinyl)benzene allow for faster flow rates and shorter processing times than can be achieved with agarose. Where the polypeptide variant comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the polypeptide variant to be recovered.

Following any preliminary purification step(s), the mixture comprising the polypeptide variant of interest and contaminants may be subjected to low pH hydrophobic interaction chromatography using an elution buffer at a pH between about 2.5–4.5, preferably performed at low salt concentrations (e.g.,from about 0–0.25M salt).

E. Pharmaceutical Formulations

Therapeutic formulations of the polypeptide variant are prepared for storage by mixing the polypeptide variant having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the polypeptide variant, which matrices are in the form of shaped articles, e.g., films, or microcapsule. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

F. Non-Therapeutic Uses for the Polypeptide Variant

The polypeptide variant of the invention may be used as an affinity purification agent. In this process, the polypeptide variant is immobilized on a solid phase such a Sephadex resin or filter paper, using methods well known in the art. The immobilized polypeptide variant is contacted with a sample containing the antigen to be purified, and thereafter the support is washed with a suitable solvent that will remove substantially all the material in the sample except the antigen to be purified, which is bound to the immobilized polypeptide variant. Finally, the support is washed with another suitable solvent, such as glycine buffer, pH 5.0, that will release the antigen from the polypeptide variant.

The polypeptide variant may also be useful in diagnostic assays, e.g., for detecting expression of an antigen of interest in specific cells, tissues, or serum.

For diagnostic applications, the polypeptide variant typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The polypeptide variant can be labeled with the radioisotope using the techniques described in Current Protocols in Immunology, Volumes 1 and 2, Coligen et al., Ed. Wiley-Interscience, New York, N.Y., Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the polypeptide variant using the techniques disclosed in Current Protocols in Immunology, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym. (ed J. Langone & H. Van Vunakis), Academic press, New York, 73:147–166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g.,orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the polypeptide variant. The skilled artisan will be aware of various techniques for achieving this. For example, the polypeptide variant can be conjugated with biotin and any of the three broad categories of labels mentioned above can be conjugated with avidin, or vice versa. Biotin binds selectively to avidin and thus, the label can be conjugated with the polypeptide variant in this indirect manner. Alternatively, to achieve indirect conjugation of the label with the polypeptide variant, the polypeptide variant is conjugated with a small hapten (e.g., digoxin) and one of the different types of labels mentioned above is conjugated with an anti-hapten polypeptide variant (e.g., anti-digoxin antibody). Thus, indirect conjugation of the label with the polypeptide variant can be achieved.

In another embodiment of the invention, the polypeptide variant need not be labeled, and the presence thereof can be detected using a labeled antibody which binds to the polypeptide variant.

The polypeptide variant of the present invention may be employed in any known assay method, such as competitive binding assays, direct and indirect sandwich assays, and immunoprecipitation assays. Zola, *Monoclonal Antibodies: A Manual of Techniques*, pp.147–158 (CRC Press, Inc. 1987).

The polypeptide variant may also be used for in vivo diagnostic assays. Generally, the polypeptide variant is labeled with a radionuclide (such as $^{111}In$, $^{99}Tc$, $^{14}C$, $^{131}I$, $^{125}I$, $^{3}H$, $^{32}P$ or 35S) so that the antigen or cells expressing it can be localized using immunoscintiography.

G. In Vivo Uses for the Polypeptide Variant

It is contemplated that the polypeptide variant of the present invention may be used to treat a mammal e.g. a patient suffering from a disease or disorder who could benefit from administration of the polypeptide variant. The conditions which can be treated with the polypeptide variant are many and include cancer (e.g. where the polypeptide variant binds the HER2 receptor or CD20); allergic conditions such as asthma (with an anti-IgE antibody); and LFA-mediated disorders (e.g. where the polypeptide variant is an anti-LFA-1 or anti-ICAM-1 antibody) etc. Where the polypeptide variant does not bind complement, but retains FcR binding capability, exemplary diseases or disorders to be treated include: cancer (e.g. where ADCC function is desirable, but complement activation would lead to amplified side effects, such as vasculitis in the blood vessels at the tumor site); disorders treated with an agonist antibody; disorders wherein the polypeptide variant binds a soluble antigen and wherein stoichiometry leads to immune complexes which activate the complement cascade and result in unwanted side effects; conditions employing an antagonist antibody which downmodulates receptor function without damaging tissue or organ function; intravenous immunoglobulin treatment for, e.g., immunodeficient individuals with autoimmune disorders.

The polypeptide variant is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the polypeptide variant is suitably administered by pulse infusion, particularly with declining doses of the polypeptide variant. Preferably the dosing is given by injections, most preferably intravenous or subcutaneous injections, depending in part on whether the administration is brief or chronic.

For the prevention or treatment of disease, the appropriate dosage of polypeptide variant will depend on the type of disease to be treated, the severity and course of the disease, whether the polypeptide variant is administered for preventive or therapeutic purposes, previous therapy, the patient's clinical history and response to the polypeptide variant, and the discretion of the attending physician. The polypeptide variant is suitably administered to the patient at one time or over a series of treatments.

Depending on the type and severity of the disease, about 1 $\mu$g/kg to 15 mg/kg (e.g., 0.1–20 mg/kg) of polypeptide variant is an initial candidate dosage for administration to the patient, whether, for example, by one or more separate administrations, or by continuous infusion. A typical daily dosage might range from about 1 $\mu$g/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

The polypeptide variant composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the polypeptide variant to be administered will be governed by such considerations, and is the minimum amount necessary to prevent, ameliorate, or treat a disease or disorder. The polypeptide variant need not be, but is optionally formulated with one or more agents currently used to prevent or treat the disorder in question. The effective amount of such other agents depends on the amount of polypeptide variant present in the formulation, the type of disorder or treatment, and other factors discussed above. These are generally used in the same dosages and with administration routes as used hereinbefore or about from 1 to 99% of the heretofore employed dosages.

The invention will be more fully understood by reference to the following examples. They should not, however, be construed as limiting the scope of this invention. All literature and patent citations mentioned herein are expressly incorporated by reference.

EXAMPLE 1

Low Affinity Receptor Binding Assay

This assay determines binding of an IgG Fc region to recombinant Fc$\gamma$RIIa, Fc$\gamma$RIIIb and Fc$\gamma$RIIIa $\alpha$ subunits expressed as His6-glutathione S transferase (GST)-tagged fusion proteins. Since the affinity of the Fc region of IgG1 for the Fc$\gamma$RI is in the nanomolar range, the binding of IgG1 Fc mutants can be measured by titrating monomeric IgG and measuring bound IgG with a polyclonal anti-IgG in a standard ELISA format (Example 2 below). The affinity of the other members of the Fc$\gamma$R family, i.e. Fc$\gamma$IIa, Fc$\gamma$RIIb and Fc$\gamma$RIIIa for IgG is however in the micromolar range and binding of monomeric IgG1 for these receptors can not be reliably measured in an ELISA format.

The following assay utilizes Fc mutants of recombinant anti-IgE E27 (FIGS. 4A and 4B) which, when mixed with human IgE at a 1:1 molar ratio, forms a stable hexamer consisting of three anti-IgE molecules and three IgE molecules. A recombinant chimeric form of IgE (chimeric IgE) was engineered and consists of a human IgE Fc region and the Fab of an anti-VEGF antibody (Presta et al. *Cancer Research* 57:4593–4599 (1997)) which binds two VEGF molecules per mole of anti-VEGF. When recombinant human VEGF is added at a 2:1 molar ratio to chimeric IgE:E27 hexamers, the hexamers are linked into larger molecular weight complexes via the chimeric IgE Fab-:VEGF interaction. The E27 component of this complex binds to the Fc$\gamma$RIIa, Fc$\gamma$RIIb and Fc$\gamma$RIIIa $\alpha$ subunits with higher avidity to permit detection in an ELISA format.

MATERIALS AND METHODS

Receptor Coat: Fc$\gamma$ receptor $\alpha$ subunits were expressed as GST fusions of His6 tagged extracellular domains (ECDs) in 293 cells resulting in an ECD-6His-GST fusion protein (Graham et al. *J. Gen. Virol.* 36:59–72 (1977) and Gorman et al. *DNA Prot. Eng. Tech.* 2:3–10 (1990)) and purified by Ni-NTA column chromatography (Qiagen, Australia) and buffer exchanged into phosphate buffered saline (PBS). Concentrations were determined by absorption at 280 nm using extinction coefficients derived by amino acid composition analysis. Receptors were coated onto Nunc F96 maxisorb plates (cat no. 439454) at 100 ng per well by adding 100 $\mu$l of receptor-GST fusion at 1 $\mu$g/ml in PBS and incubated for 48 hours at 4° C. Prior to assay, plates were washed 3× with 250 $\mu$l of wash buffer (PBS pH 7.4 containing 0.5% TWEEN 20™) and blocked with 250 $\mu$l of assay buffer (50 mM Tris buffered saline, 0.05% TWEEN 20™, 0.5% RIA grade bovine albumin (Sigma A7888, and 2 mM EDTA pH 7.4).

Immune Complex Formation: Equal molar amounts (1:1) of E27 and recombinant chimeric IgE which binds two moles recombinant human VEGF per mole of chimeric IgE are added to a 12×75mm polypropylene tube in PBS and mixed by rotation for 30 minutes at 25° C. E27 (anti-IgE)/ chimeric IgE (IgE) hexamers are formed during this incubation. Recombinant human VEGF (165 form, MW 44,000) is added at a 2:1 molar ratio to the IgE concentration and mixed by rotation an additional 30 minutes at 25° C. VEGF-chimeric IgE binding links E27:chimeric IgE hexamers into larger molecular weight complexes which bind FcγR α subunit ECD coated plates via the Fc region of the E27 antibody.

E27:chimeric IgE:VEGF (1:1:2 molar ratio) complexes are added to FcγR α subunit coated plates at E27 concentrations of 5 μg and 1 μg total IgG in quadruplicate in assay buffer and incubated for 120 minutes at 25° C. on an orbital shaker.

Complex Detection: Plates are washed 5× with wash buffer to remove unbound complexes and IgG binding is detected by adding 100 μl horse radish peroxidase (HRP) conjugated goat anti-human IgG (γ) heavy chain specific (Boehringer Mannheim 1814249) at 1:10,000 in assay buffer and incubated for 90min at 25° C. on an orbital shaker. Plates are washed 5× with wash buffer to remove unbound HRP goat anti-human IgG and bound anti-IgG is detected by adding 100 μl of substrate solution (0.4mg/ml o-phenylenedaimine dihydrochloride, Sigma P6912, 6 mM $H_2O_2$ in PBS) and incubating for 8 min at 25° C. Enzymatic reaction is stopped by the addition of 100 μl 4.5N $H_2SO_4$ and colorimetric product is measured at 490 nm on a 96 well plate densitometer (Molecular Devices). Binding of E27 mutant complexes is expressed as a percent of the wild type E27 containing complex.

EXAMPLE 2

Identification of Unique C1q Binding Sites in a Human IgG Antibody

In the present study, mutations were identified in the CH2 domain of a human IgG1 antibody, "C2B8" (Reff et al., *Blood* 83:435 (1994)), that ablated binding of the antibody to C1q but did not alter the conformation of the antibody nor affect binding to each of the FcγRs. By alanine scanning mutagenesis, five mutants in human IgG1 were identified, D270K, D270V, K322A P329A, and P331, that were non-lytic and had decreased binding to C1q. The data suggested that the core C1q binding sites in human IgG1 is different from that of murine IgG2b. In addition, K322A, P329A and P331A were found to bind normally to the CD20 antigen, and to four Fc receptors, FcγRI, FcγRII, FcγRIII and FcRn.

MATERIALS AND METHODS

Construction of C2B8 Mutants: The chimeric light and heavy chains of anti-CD20 antibody C2B8 (Reff et al., *Blood* 83:435 (1994)) subcloned separately into previously described PRK vectors (Gorman et al., *DNA Protein Eng. Tech.* 2:3 (1990)) were used. By site directed mutagenesis (Kunkel et al., *Proc. Natl. Acad.Sci.USA* 82:488 (1985)), alanine scan variants of the Fc region in the heavy chain were constructed. The heavy and light chain plasmids were co-transfected into an adenovirus transformed human embryonic kidney cell line as previously described (Werther et al., *J. Immunol.* 157:4986 (1996)). The media was changed to serum-free 24 hours after transfection and the secreted antibody was harvested after five days. The antibodies were purified using Protein A-SEPHAROSE CL-4B™ (Pharmacia), buffer exchanged and concentrated to 0.5 ml with PBS using a Centricon-30 (Amicon), and stored at 4° C. The concentration of the antibody was determined using total Ig-binding ELISA.

C1q Binding ELISA: Costar 96 well plates were coated overnight at 4° C. with the indicated concentrations of C2B8 in coating buffer (0.05 M sodium carbonate buffer), pH 9. The plates were then washed 3× with PBS/0.05% TWEEN 20™, pH 7.4 and blocked with 200 μl of ELISA diluent without thimerosal (0.1M NaPO4/0.1M NaCl/0.1% gelatin/ 0.05% TWEEN 20™/0.05% ProClin300) for 1 hr at room temperature. The plate was washed 3× with wash buffer, an aliquot of 100 μl of 2 μg/ml C1q (Quidel, San Diego, Calif.) was added to each well and incubated for 2 hrs at room temperature. The plate was then washed 6× with wash buffer. 100 μl of a 1:1000 dilution of sheep anti-complement C1q peroxidase conjugated antibody (Biodesign) was added to each well and incubated for 1 hour at room temperature. The plate was again washed 6× with wash buffer and 100 μl of substrate buffer (PBS/0.012% $H_2O_2$) containing OPD (O-phenylenediamine dihydrochloride (Sigma)) was added to each well. The oxidation reaction, observed by the appearance of a yellow color, was allowed to proceed for 30 minutes and stopped by the addition of 100 μl of 4.5 N $H_2SO_4$. The absorbance was then read at (492–405) nm using a microplate reader (SPECTRA MAX 250™, Molecular Devices Corp.). The appropriate controls were run in parallel (ie. the ELISA was performed without C1q for each concentration of C2B8 used and also the ELISA was performed without C2B8). For each mutant, C1q binding was measured by plotting the absorbance (492–405) nm versus concentration of C2B8 in μg/ml using a 4-parameter curve fitting program (KALEIDAGRAPH™) and comparing $EC_{50}$ values.

Complement Dependent Cytotoxicity (CDC) Assay: This assay was performed essentially as previously described (Gazzano-Santoro et al., *J. Immunol. Methods* 202:163 (1997)). Various concentrations of C2B8 (0.08–20 μg/ml) were diluted with RHB buffer (RPMI 1640/20 mM HEPES (pH 7.2)/2 mM Glutamine/0.1% BSA/100 μg/ml Gentamicin). Human complement (Quidel) was diluted 1:3 in RHB buffer and WIL2-S cells (available from the ATCC, Manassas, Va.) which express the CD20 antigen were diluted to a density of 1×10⁶ cells /ml with RHB buffer. Mixtures of 150 μl containing equal volumes of C2B8, diluted human complement and WIL2-S cells were added to a flat bottom tissue culture 96 well plate and allowed to incubate for 2 hrs at 37° C. and 5% $CO_2$ to facilitate complement mediated cell lysis. 50 μl of alamar blue (Accumed International) was then added to each well and incubated overnight at 37° C. The absorbance was measured using a 96-well fluorometer with excitation at 530 nm and emission at 590 nm. As described by Gazzano-Santoro et al., the results are expressed in relative fluorescence units (RFU). The sample concentrations were computed from a C2B8 standard curve and the percent activity as compared to wild type C2B8 is reported for each mutant.

CD20 Binding Potency of the C2B8 Mutants: The binding of C2B8 and mutants to the CD20 antigen were assessed by a method previously described (Reff et al., (1994), supra; reviewed in Gazzano-Santoro et al., (1996), supra). WIL2-S cells were grown for 3–4 days to a cell density of 1×10⁶ cells/ml. The cells were washed and spun twice in FACS buffer (PBS/0.1% BSA/0.02% $NaN_3$) and resuspended to a cell density of 5×10⁶ cells/ml. 200 μl of cells (5×10⁶ cells/ml) and 20 μl of diluted C2B8 samples were added to a 5 ml tube and incubated at room temperature for 30 minutes with agitation. The mixture was then washed with 2 ml of cold FACS buffer, spun down and resuspended in 200 μl of cold FACS buffer. To the suspension, 10 μl of goat anti-human IgG-FITC (American Qualex Labs.) was added and the mixture was incubated in the dark at room temperature for 30 minutes with agitation. After incubation, the mixture was washed with 2 ml of FACS buffer, spun down and resuspended in 1 ml of cold fixative buffer (1% formaldehyde in PBS). The samples were analyzed by flow cytometry and the results expressed as relative fluorescence units (RFU) were plotted against antibody concentrations using a 4-parameter curve fitting program (KALEIDAGRAPH™). The $EC_{50}$ values are reported as a percentage of that of the C2B8 reference material.

FcγR Binding ELISAs: FcγRI α subunit-GST fusion was coated onto Nunc F96 maxisorb plates (cat no. 439454) by adding 100 μl of receptor-GST fusion at 1 μg/ml in PBS and incubated for 48 hours at 4° C. Prior to assay, plates are washed 3× with 250 μl of wash buffer (PBS pH 7.4 containing 0.5% TWEEN 20™) and blocked with 250 μl of assay buffer (50 mM Tris buffered saline, 0.05% TWEEN 20™, 0.5% RIA grade bovine albumin (Sigma A7888), and 2 mM EDTA pH 7.4). Samples diluted to 10 μg/ml in 1 ml of assay buffer are added to FcγRI α subunit coated plates and incubated for 120 minutes at 25° C. on an orbital shaker. Plates are washed 5× with wash buffer to remove unbound complexes and IgG binding is detected by adding 100 μl horse radish peroxidase (HRP) conjugated goat anti-human IgG (γ) heavy chain specific (Boehringer Mannheim 1814249) at 1:10,000 in assay buffer and incubated for 90 min at 25° C. on an orbital shaker. Plates are washed 5× with wash buffer to remove unbound HRP goat anti-human IgG and bound anti-IgG is detected by adding 100 μl of substrate solution (0.4 mg/ml o-phenylenedaimine dihydrochloride, Sigma P6912, 6 mM $H_2O_2$ in PBS) and incubating for 8 min at 25° C. Enzymatic reaction is stopped by the addition of 100 μl 4.5N $H_2SO_4$ and calorimetric product is measured at 490 nm on a 96 well plate densitometer (Molecular Devices). Binding of variant is expressed as a percent of the wild type molecule.

FcγRII and III binding ELISAs were performed as described in Example 1 above.

For measuring FcRn binding activity of IgG variants, ELISA plates were coated with 2 μg/ml streptavidin (Zymed, South San Francisco) in 50 mM carbonate buffer, pH 9.6, at 4° C. overnight and blocked with PBS-0.5% BSA, pH 7.2 at room temperature for one hour. Biotinylated FcRn (prepared using biotin-X-NHS from Research Organics, Cleveland, Ohio and used at 1–2 μg/ml) in PBS-0.5% BSA, 0.05% polysorbate 20, pH 7.2, was added to the plate and incubated for one hour. Two fold serial dilutions of IgG standard (1.6–100 ng/ml) or variants in PBS-0.5% BSA, 0.05% polysorbate 20, pH 6.0, were added to the plate and incubated for two hours. Bound IgG was detected using peroxidase labeled goat F(ab')$_2$ anti-human IgG F(ab')$_2$ in the above pH 6.0 buffer (Jackson Immunoresearch, West Grove, Pa.) followed by 3,3',5,5'-tetramethyl benzidine (Kirgaard & Perry Laboratories) as the substrate. Plates were washed between steps with PBS-0.05% polysorbate 20 at either pH 7.2 or 6.0. Absorbance was read at 450 nm on a Vmax plate reader (Molecular Devices, Menlo Park, Calif.). Titration curves were fit with a four-parameter nonlinear regression curve-fitting program (KaleidaGraph, Synergy software, Reading, Pa.). Concentrations of IgG variants corresponding to the mid-point absorbance of the titration curve of the standard were calculated and then divided by the concentration of the standard corresponding to the mid-point absorbance of the standard titration curve.

RESULTS AND DISCUSSION

By alanine scanning mutagenesis, several single point mutations were constructed in the CH2 domain of C2B8 beginning with E318A, K320A and K322A. All the mutants constructed bound normally to the CD20 antigen (Table 1).

TABLE 1

|        | wt  | E318A | K320A | K322A | P329A | P331A |
|--------|-----|-------|-------|-------|-------|-------|
| FcRn   | +   | +     | +     | +     |       |       |
| CD20   | +   | +     | +     | +     | +     | +     |
| FcγRI  | +   | +     | +     | +     | +     | +     |
| FcγRII | +   | +     | +     | +     | +     | +     |
| FcγRIII| +   | +     | +     | +     | +     | +     |
| *C1q   | +++ | ++    | +++   | −     | −     | −     |
| CDC    | +   | +     | +     | −     | −     | −     |

Figure 2:
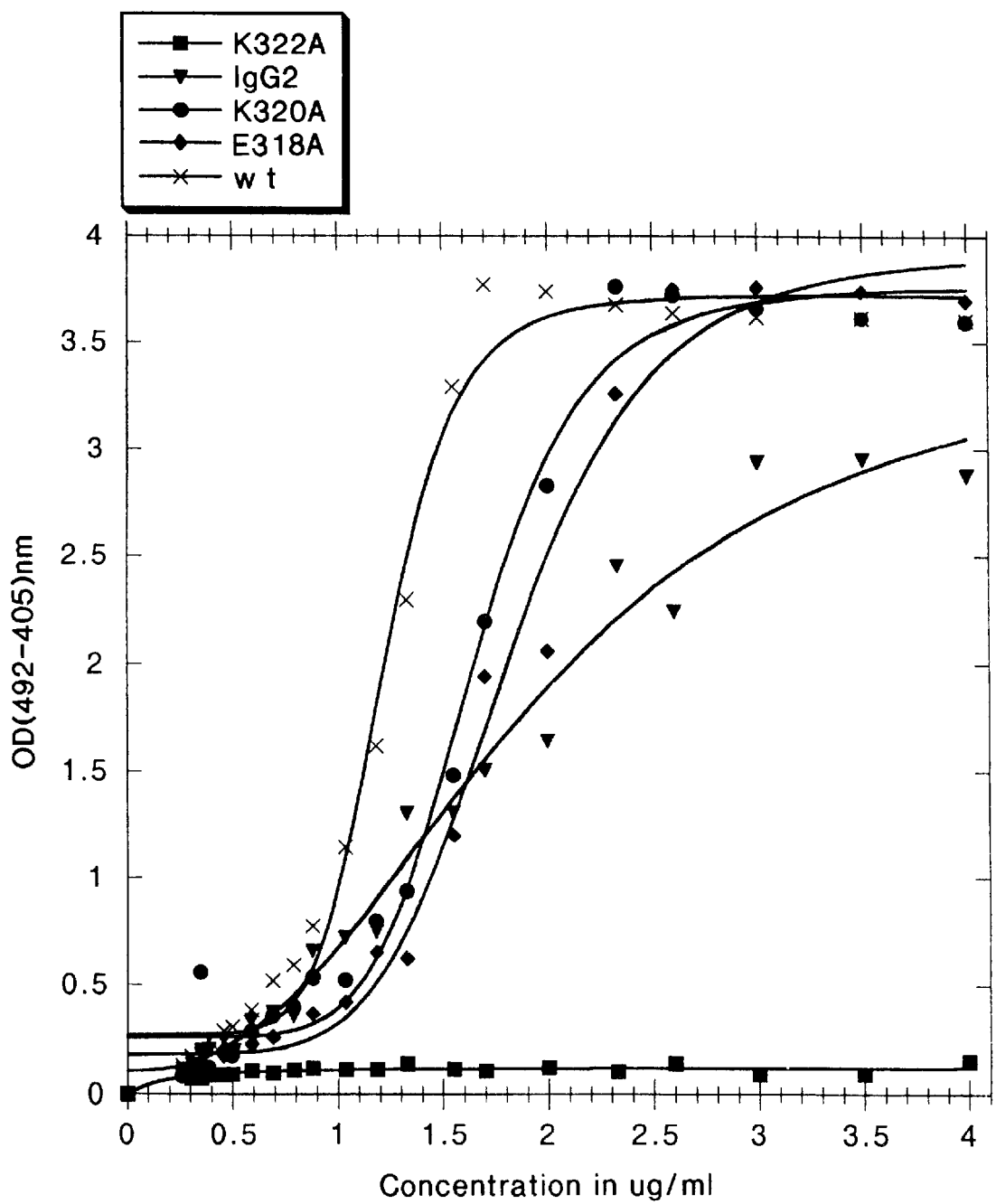
FIG. 2 shows C1q binding of wild type (wt) C2B8 antibody; C2B8 antibody with a human IgG2 constant region (IgG2); and mutants K322A, K320A and E318A.

(+) indicates binding and (−) signifies binding abolished
*With respect to C1q binding, each + sign is equivalent to approximately 33% binding.

Where binding of human complement to an antibody with a human Fc was analyzed, the ability of E318A and K320A to activate complement was essentially identical to that of wild type C2B8 (Table 1). When compared to wild type C2B8, there appears to be little difference in the binding of E318A and K320A to C1q. There is only a 10% decrease in the binding of K320A and about a 30% decrease in the binding of E318A to C1q (FIG. 2). The results indicate that the effect of the E318A and the K320A substitution on complement activation and C1q binding is minimal. Also, the human IgG1 of C2B8 was substituted for human IgG2 and used as a negative control in the C1q binding studies. The IgG2 mutant appears to have a much lower affinity for C1q than the E318A and K320A mutants (FIG. 2). Thus, the results demonstrate that E318 and K320 do not constitute the core C1q binding sites for human IgG1. Conversely, the K322A substitution had a significant effect on both complement activity and C1q binding. The K322A mutant did not have CDC activity when tested in the above CDC assay and was more than a 100 fold lower than wild type C2B8 in binding to C1q (FIG. 2). In the human system, K322 is the only residue of the proposed core C1q binding sites that appeared to have a significant effect on complement activation and C1q binding.

Figure 3:
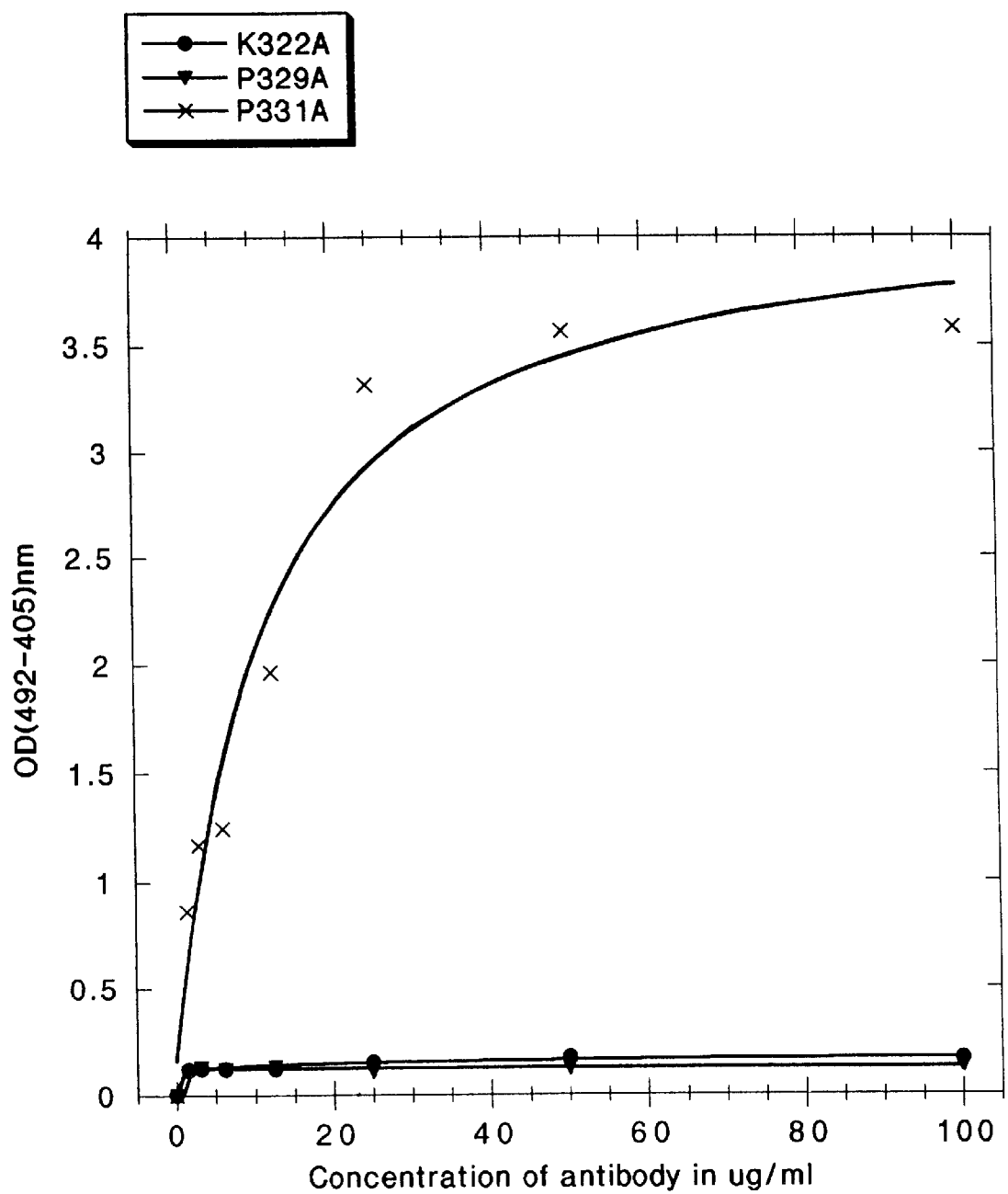
FIG. 3 depicts C1q binding of mutants P331 A, P329A and K322A.

Since the Duncan and Winter study was performed using mouse IgG2b and the above results reveal that K320 and E318 in human IgG1 are not involved in C1q binding, and without being bound to any one theory, the above data suggest that the C1q binding region in murine IgGs is different from that of the human. To investigate this further and also to identify additional mutants that do not bind to C1q and hence do not activate complement, several more point mutations in the vicinity of K322 were constructed as assessed from the three dimensional structure of the C2B8 Fc. Mutants constructed, K274A, N276A, Y278A, S324A, P329A, P331A, K334A, and T335A, were assessed for their ability to bind C1q and also to activate complement. Many of these substitutions had little or no effect on C1q binding or complement activation. In the above assays, the P329A and the P331A mutants did not activate complement and had decreased binding to C1q. The P331A mutant did not activate complement and was 60 fold lower in binding to C1q (FIG. 3) when compared to wild type C2B8 (FIG. 2). The concentration range of the antibody variants used in FIG. 3 is expanded to 100 μg/ml in order to observe saturation of C1q binding to the P331A variant. The mutation P329A results in an antibody that does not activate complement and is more than a 100 fold lower in binding to C1q (FIG. 3) when compared to wild type C2B8 (FIG. 2).

Mutants that did not bind to C1q and hence did not activate complement were examined for their ability to bind to the Fc receptors: FcγRI, FcγRIIa, FcγRIIb, FcγRIIIa and FcRn. This particular study was performed using a humanized anti-IgE antibody, an IgG1 antibody with these mutations (see Example 1 above). The results revealed the mutants, K322A and P329A, bind to all the Fc receptors to the same extent as the wild type protein (Table 2). However, there was a slight decrease in the binding of P331A to FcγRIIb.

In conclusion, two amino acid substitutions in the COOH terminal region of the CH2 domain of human IgG1, K322A and P329A were identified that result in more than 100 fold decrease in C1q binding and do not activate the CDC pathway. These two mutants, K322A and P329A, bind to all Fc receptors with the same affinity as the wild type antibody. Based on the results, summarized in Table 2, and without being bound to any one theory, it is proposed that the C1q binding epicenter of human IgG1 is centered around K322, P329 and P331 and is different from the murine IgG2b epicenter which constitutes E318, K320 and K322.

TABLE 2

|  | wt | E318A | K320A | K322A | P329A | P331A |
|---|---|---|---|---|---|---|
| CD20 | 100 | 89 | 102 | 86 | 112 | 103 |
| aFCγRI | 100 | 93 | 102 | 90 | 104 | 74 |
| aFcγRIIa | 100 | 113 | 94 | 109 | 111 | 86 |
| aFCγRIIb | 100 | 106 | 83 | 101 | 96 | 58 |
| aFCγRIII | 100 | 104 | 72 | 90 | 85 | 73 |
| CDC | 100 | 108 | 108 | none | none | none | aFor binding to the FcγRs the mutants were made in the E27 background (anti-IgE). The results are presented as a percentage of the wild type.

Figure 6:
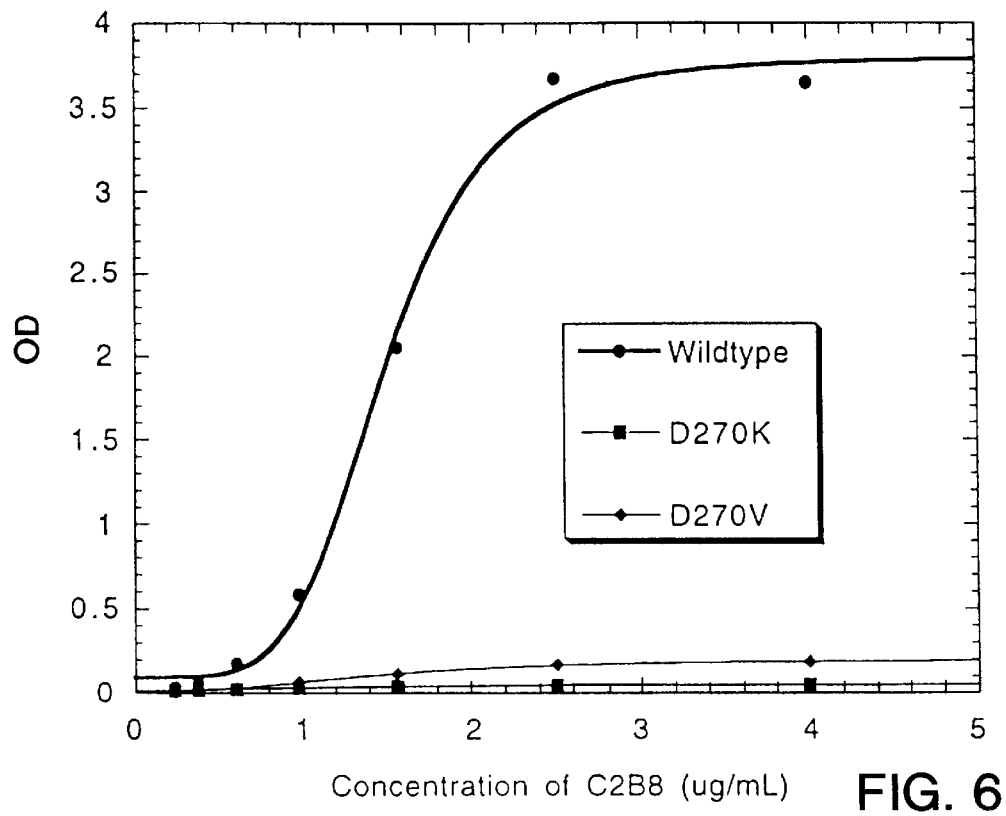
FIG. 6 shows C1q binding results obtained for mutants D270K and D270V compared to wild type C2B8.
Figure 7:
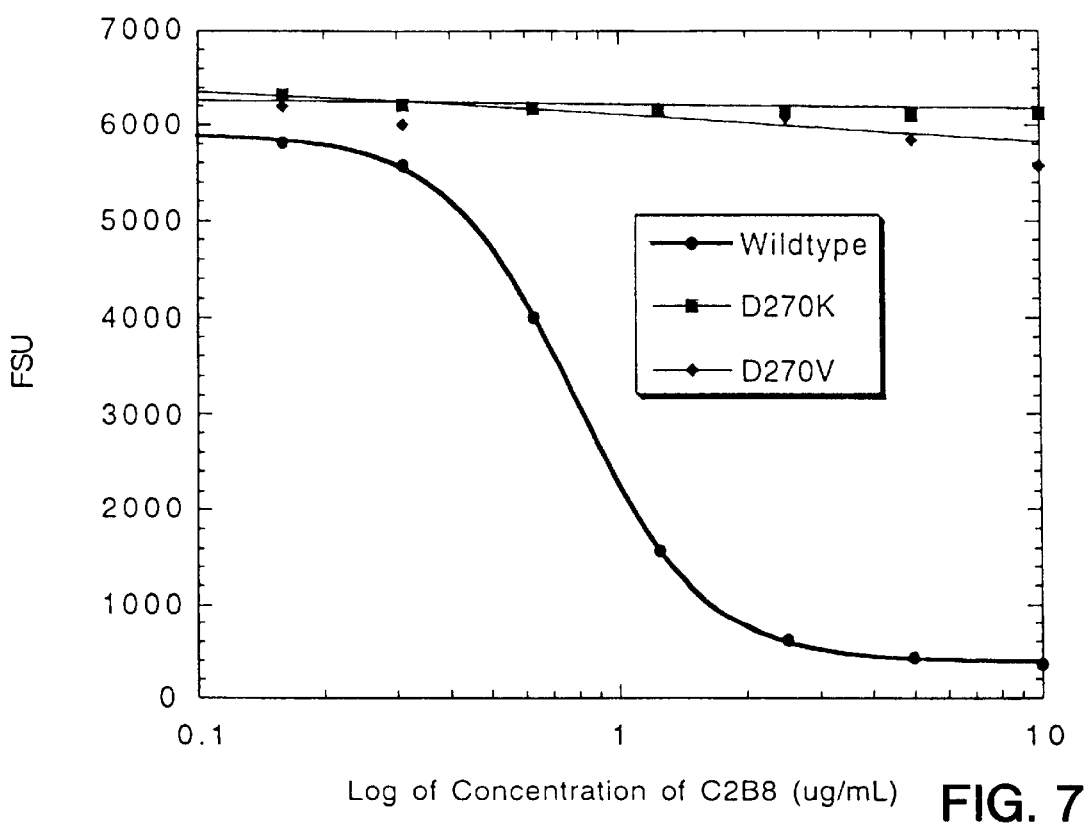
FIG. 7 depicts complement dependent cytotoxicity (CDC) of mutants D270K and D270V, compared to wild type C2B8.

A further residue involved in binding human C1q was identified using the methods described in the present example. The residue D270 was replaced with lysine and valine to generate mutants D270K and D270V, respectively. These mutants both showed decreased binding to human C1q (FIG. 6) and were non-lytic (FIG. 7). The two mutants bound the CD20 antigen normally and recruited ADCC.

EXAMPLE 3

Mutants with Improved C1q Binding

The following study shows that substitution of residues at positions K326, A327, E333 and K334 resulted in mutants with at least about a 30% increase in binding to C1q when compared to the wild type antibody. This indicated K326, A327, E333 and K334 are potential sites for improving the efficacy of antibodies by way of the CDC pathway. The aim of this study was to improve CDC activity of an antibody by increasing binding to C1q. By site directed mutagenesis at K326 and E333, several mutants with increased binding to C1q were constructed. The residues in order of increased binding at K326 are K<V<E<A<G<D<M<W, and the residues in order of increased binding at E333 are E<Q<D<V<G<A<S. Four mutants, K326M, K326D, K326E and E333S were constructed with at least a two-fold increase in binding to C1q when compared to wild type. Mutant K326W displayed about a five-fold increase in binding to C1q.

Mutants of the wild type C2B8 antibody were prepared as described above in Example 2. A further control antibody, wild type C2B8 produced in Chinese hamster ovary (CHO) cells essentially as described in U.S. Pat. No. 5,736,137, was included in a C1q binding ELISA to confirm that wt C2B8 produced in the 293 kidney cell line had the same C1q binding activity as the CHO-produced antibody (see "CHO-wt-C2B8" in FIG. 8). The C1q binding ELISA, CDC assay, and CD20 binding potency assay in this example were performed as described in Example 2 above.

Figure 8:
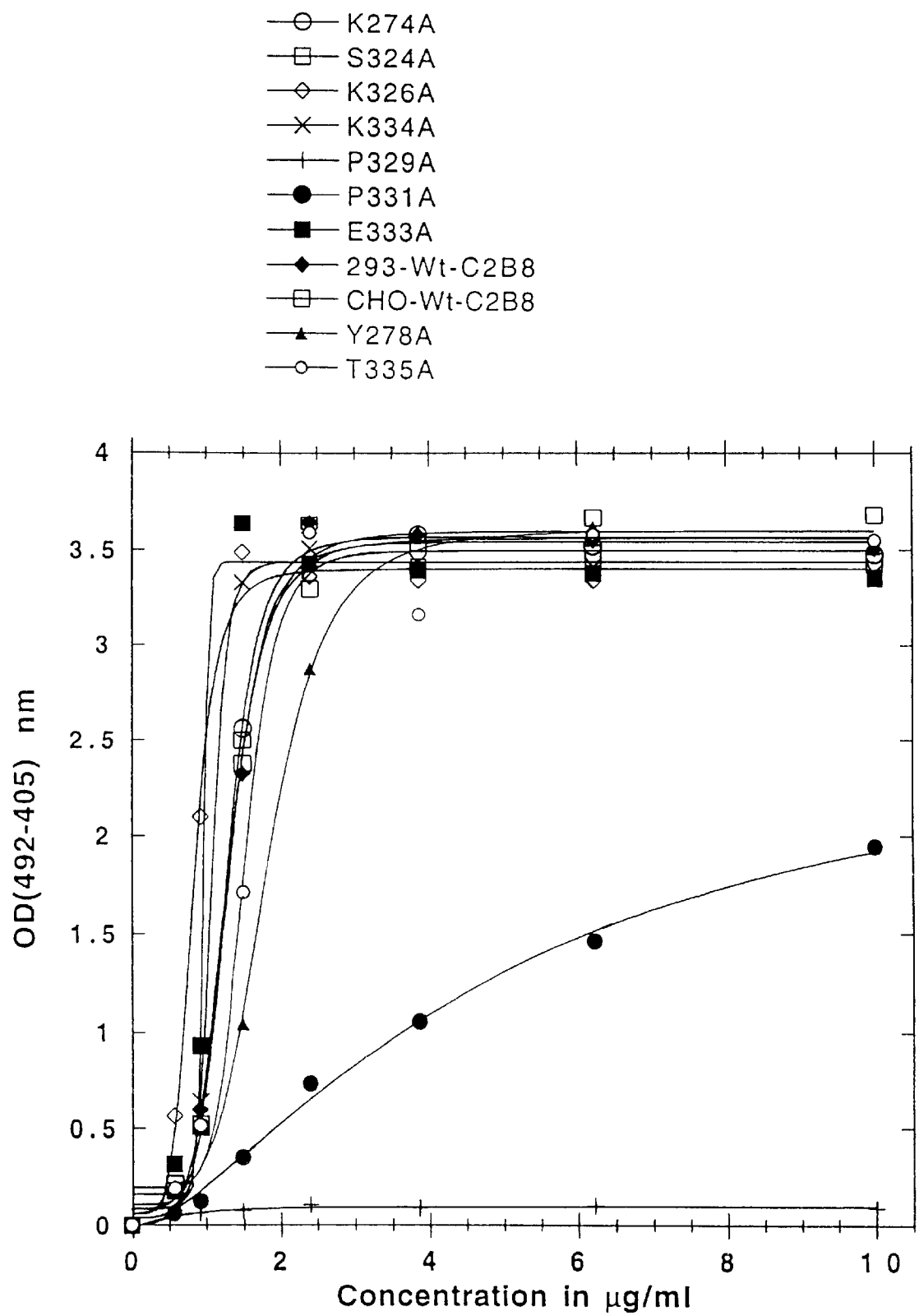
FIG. 8 shows C1q binding ELISA results for 293 cell-produced wild type C2B8 antibody (293-Wt-C2B8), CHO-produced wild type C2B8 antibody (CHO-Wt-C2B8) and various mutant antibodies.

As shown in FIG. 8, alanine substitution at K326 and E333 in C2B8 resulted in mutants with about a 30% increase in binding to C1q.

Several other single point mutants at K326 and E333 were constructed and assessed for their ability to bind C1q and activate complement. All the mutants constructed bound normally to the CD20 antigen.

Figure 9:
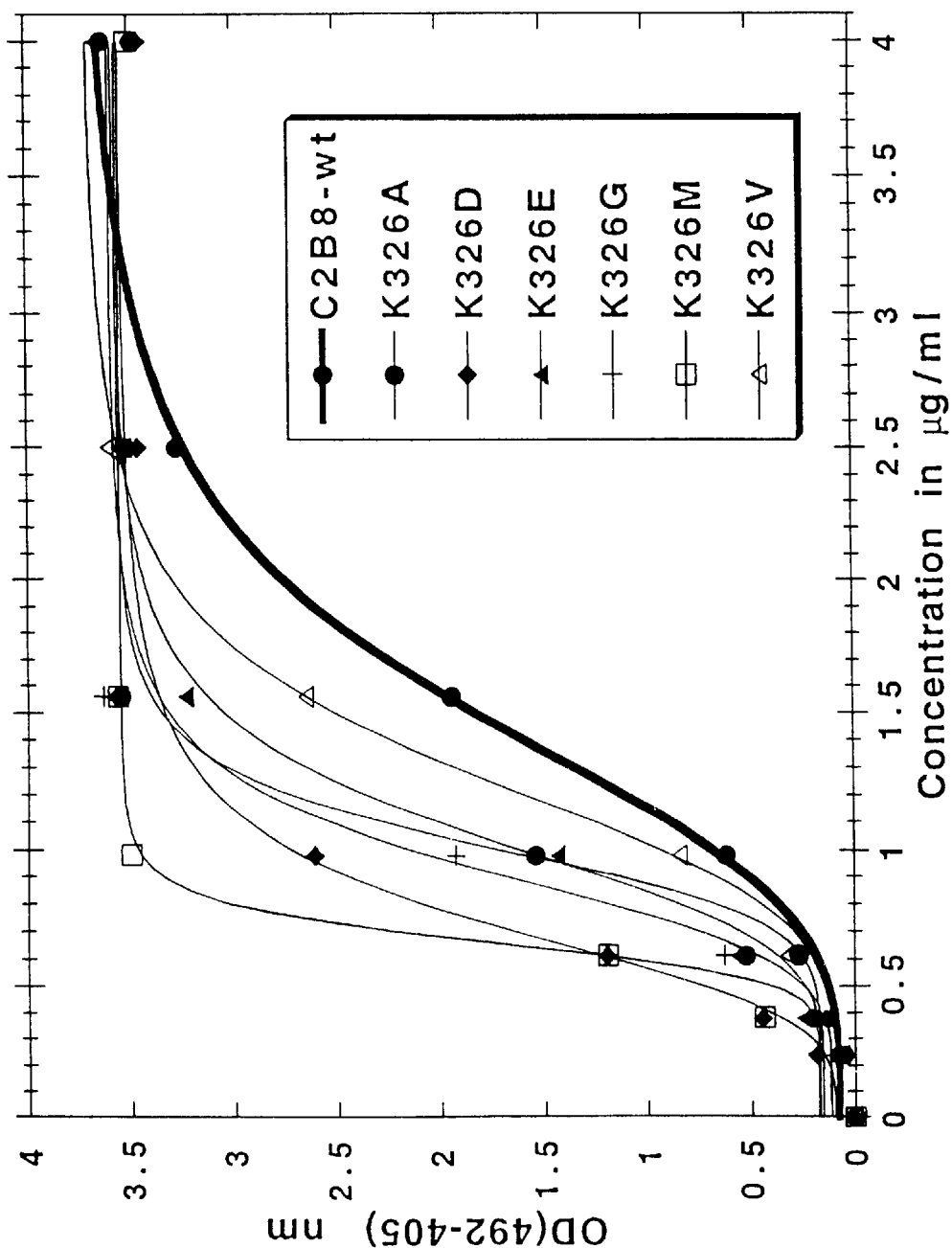
FIG. 9 shows C1q binding ELISA results obtained for wild type (wt) C2B8 and various mutant antibodies as determined in Example 3.

With respect to K326, the other single point mutants constructed were K326A, K326D, K326E, K326G, K326V, K326M and K326W. As shown in FIG. 9, these mutants all bound to C1q with a better affinity than the wild type antibody. K326W, K326M, K326D and K326E showed at least a two-fold increase in binding to C1q (Table 3). Among the K326 mutants, K326W had the best affinity for C1q.

TABLE 3

| Mutant | EC$_{50}$ value |
|---|---|
| Wild type | 1.53 |
| K326V | 1.30 |
| K326A | 1.03 |
| K326E | 1.08 |
| K326G | 0.95 |
| K326D | 0.76 |
| K326M | 0.67 |
| K326W | 0.47 |
| E333S | 0.81 |
| E333A | 0.98 |
| E333G | 1.14 |
| E333V | 1.18 |
| E333D | 1.22 |
| E333Q | 1.52 |
| K334A | 1.07 |

Figure 10:
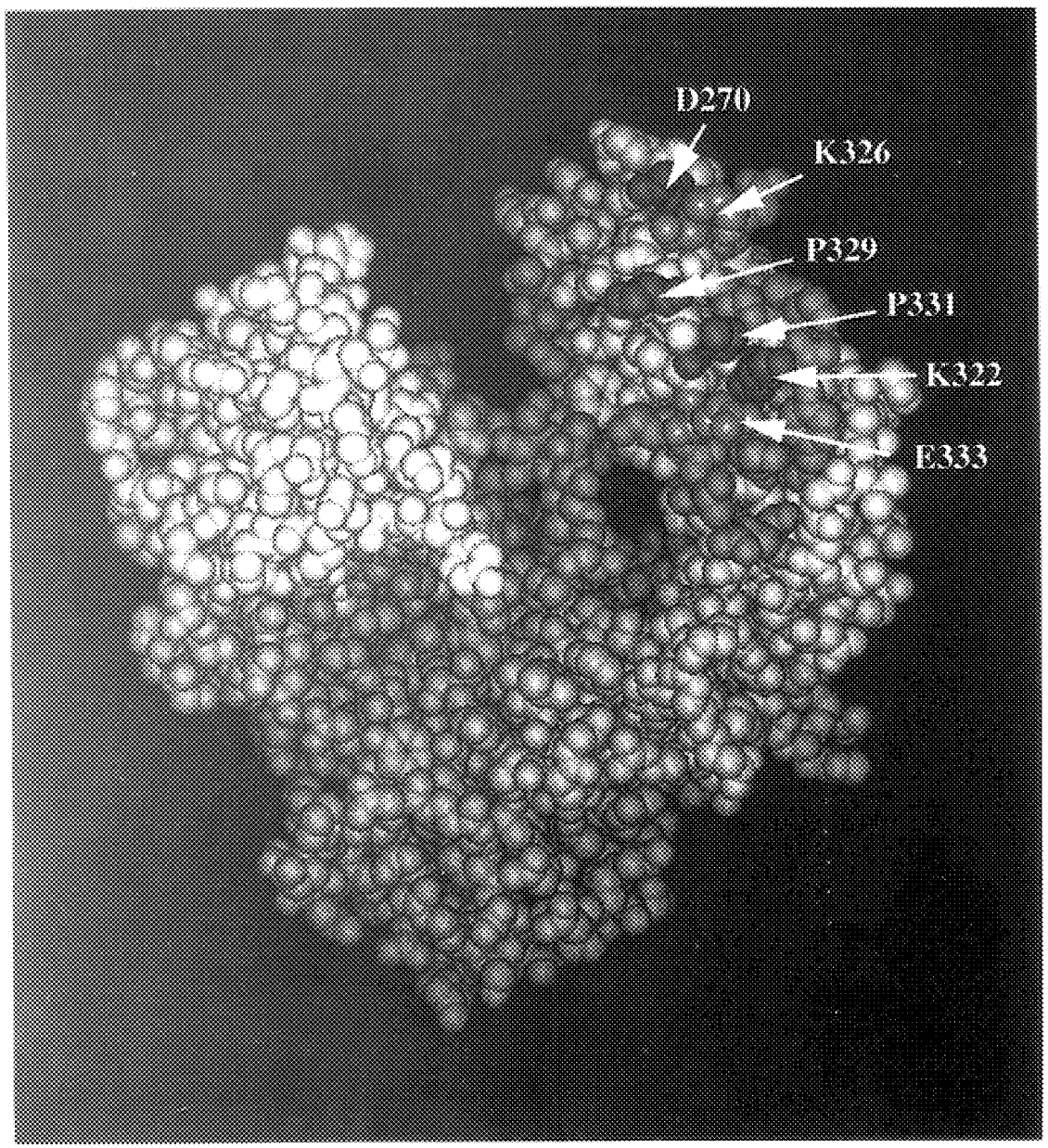
FIG. 10 depicts the three-dimensional structure of a human IgG Fc, highlighting residues: Asp270, Lys326, Pro329, Pro331, Lys322 and Glu333.

Substitutions with hydrophobic as well as charged residues resulted in mutants with increased binding to C1q. Even substitution with glycine which is known to impart flexibility to a chain and is well conserved in nature, resulted in a mutant with higher affinity for C1q when compared to the wild type. It would appear that any amino acid substitution at this site would result in a mutant with higher affinity for C1q. As assessed from the three-dimensional structure, K326 and E333 are in the vicinity of the core C1q binding sites (FIG. 10).

Figure 11:
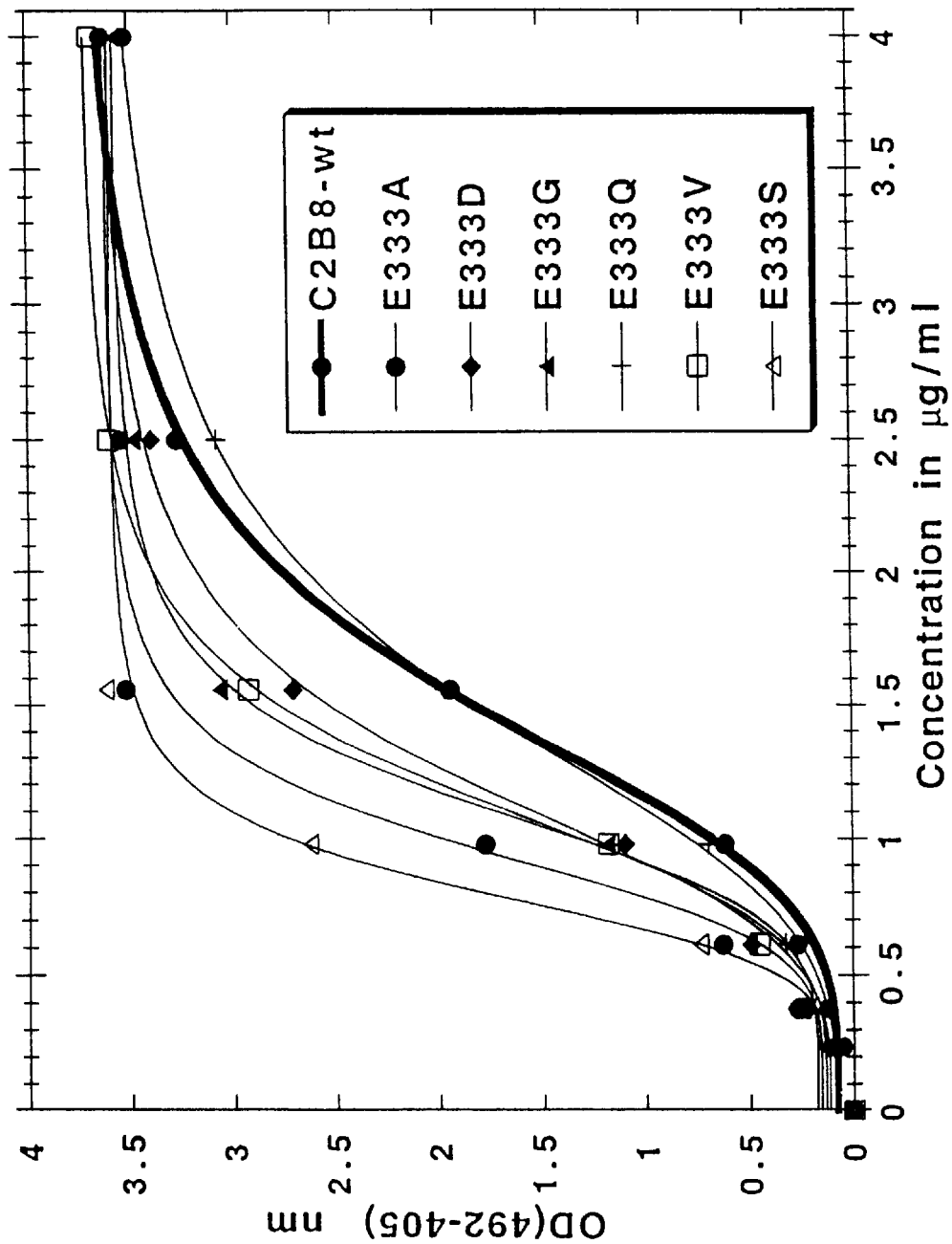
FIG. 11 shows C1q binding ELISA results obtained for wild type C2B8 and various mutant antibodies as determined in Example 3.

In addition to alanine, E333 was also substituted with other amino acid residues. These mutants, E333S, E333G, E333V, E333D, and E333Q, all had increased binding to C1q when compared to the wild type (FIG. 11). As shown in Table 3, the order of binding affinity for C1q was as follows: E333S>E333A>E333G>E333V>E333D>E333Q. Substitutions with amino acid residues with small side chain volumes, i.e. serine, alanine and glycine, resulted in mutants with higher affinity for C1q in comparison to the other mutants, E333V, E333D and E333Q, with larger side chain volumes. The mutant E333S had the highest affinity for C1q, showing a two-fold increase in binding when compared to the wild type. Without being bound to any one theory, this indicates the effect on C1q binding at 333 may also be due in part to the polarity of the residue.

Figure 12:
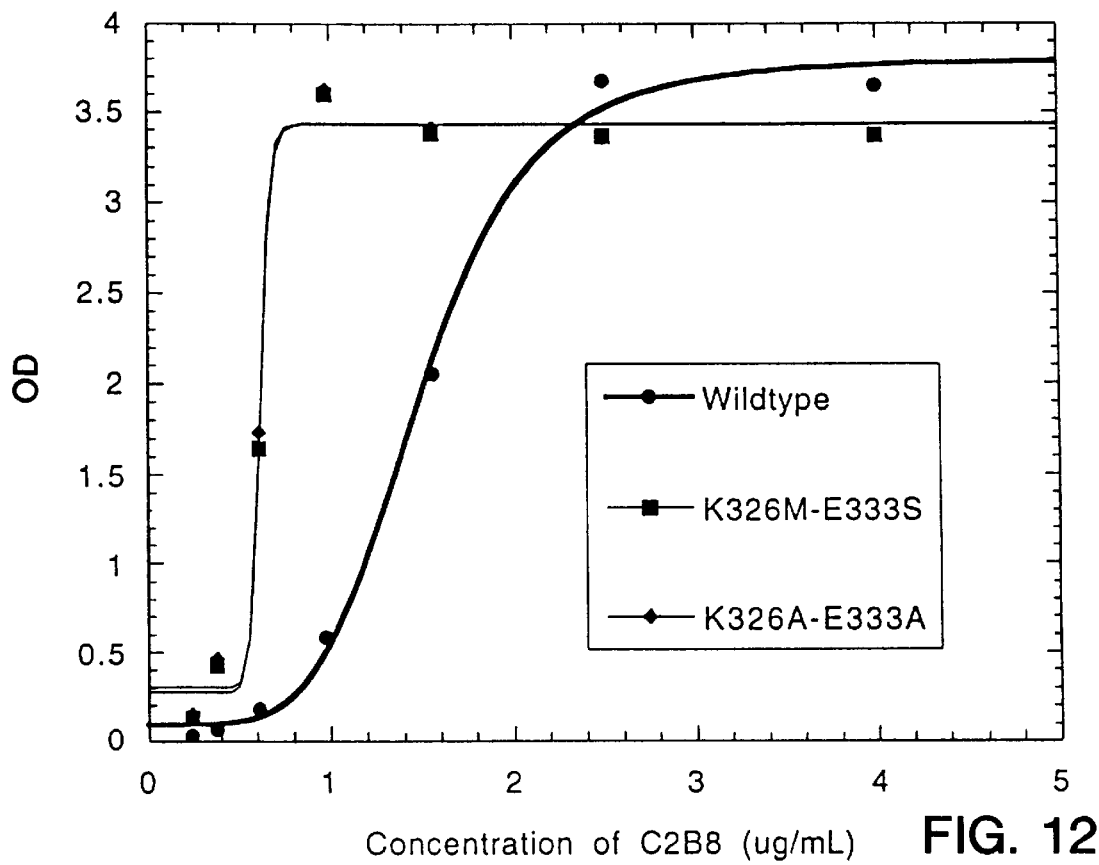
FIG. 12 shows C1q binding ELISA results obtained for wild type C2B8 and double mutants, K326M-E333S and K326A-E333A.
Figure 13:
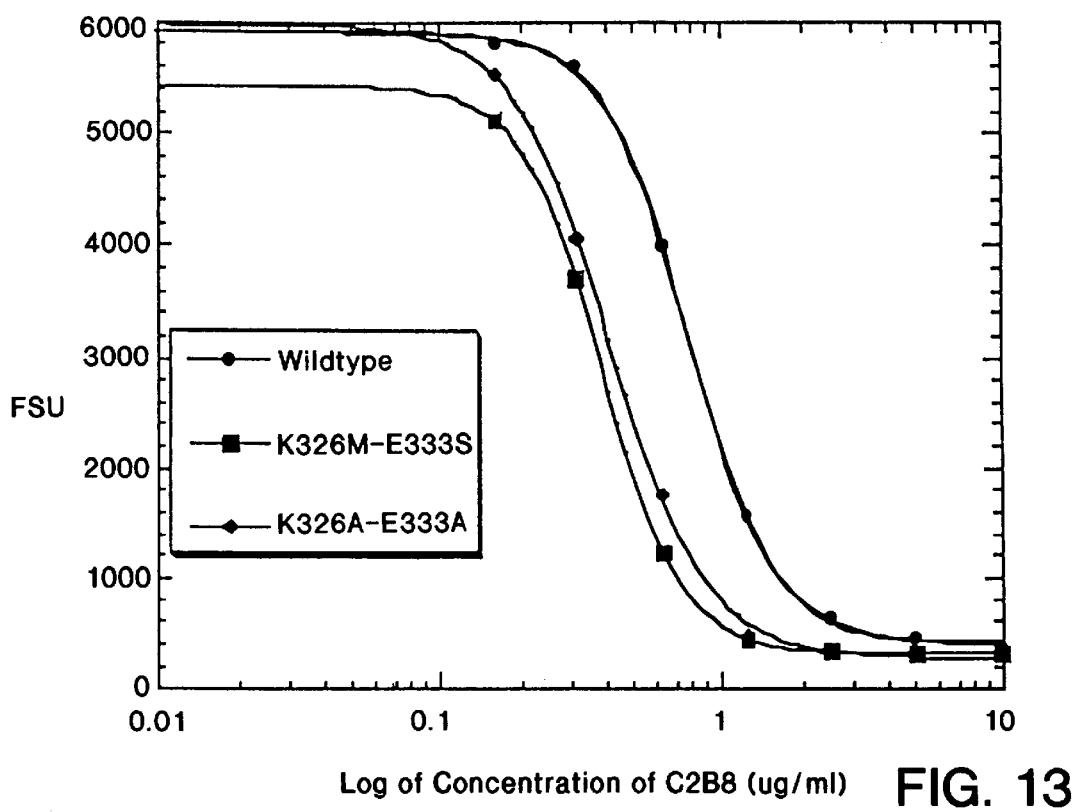
FIG. 13 shows CDC of wild type C2B8 and double mutants, K326M-E333S and K326A-E333A.

Double mutants were also generated. As shown in FIGS. 12 and 13, double mutants K326M-E333S and K326A-E333A were at least three-fold better at binding human C1q than wild type C2B8 (FIG. 12) and at least two-fold better at mediating CDC compared to wild type C2B8 (FIG. 13). Additivity indicates these are independently acting mutants.

An additional double mutant K326W-E333S was generated which was six-fold better at binding human C1q and three-fold better at mediating CDC compared to wild type C2B8. This double mutant was deficient in ADCC activity in a cell-based assay.

Figure 14:
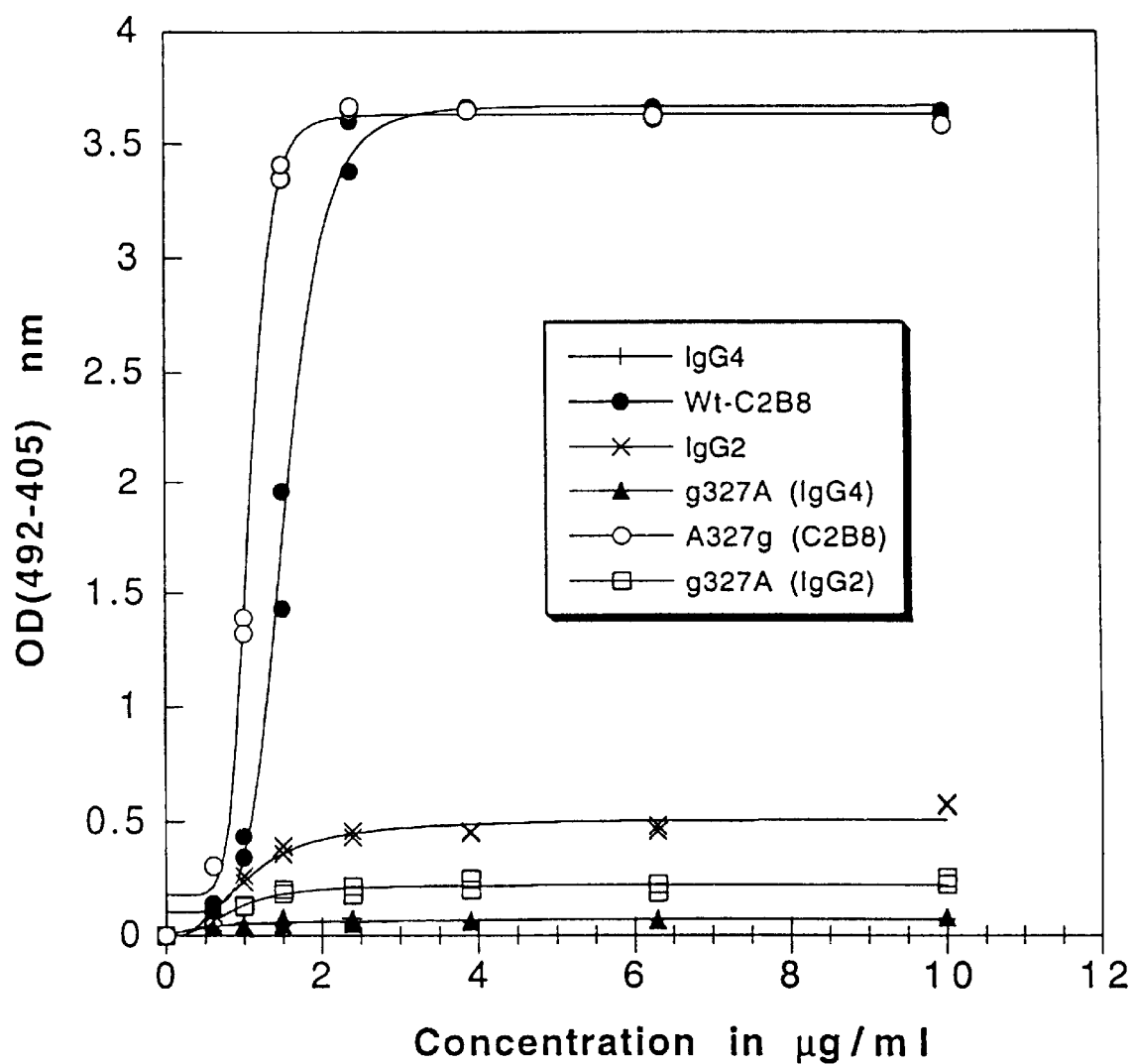
FIG. 14 depicts C1q binding ELISA results obtained for C2B8 with a human IgG4 heavy chain constant region (IgG4), wild type C2B8 (Wt-C2B8), C2B8 with a human IgG2 heavy chain constant region (IgG2), and mutant antibodies as described in Example 3.

As shown in FIG. 14, a further mutant with improved C1q binding (50% increase) was made by changing A327 in a human IgG1 constant region to glycine. Conversely, in a human IgG2 constant region, changing G327 to alanine reduced C1q binding of the IgG2 antibody.

---

What is claimed is:

1. A variant of an antibody or immunoadhesin comprising a human IgG Fcc region, which variant comprises an amino acid substitution at amino acid position 270 or 329, or at two or more of amino acid positions 270, 322, 329 and 331 of the human IgG Fc region, where the numbering of the residues in the IgG Fc region is that of the EU index as in Kabat, wherein the antibody variant is able to bind an antigen, and the immunoadhesin variant is able to bind a ligand or receptor.

2. The variant of claim 1 having Pro329 of the human IgG Fc region substituted with another amino acid.

3. The variant of claim 1 having Asp270 of the human IgG Fc region substituted with another amino acid.

4. The variant of claim 1 wherein the polypeptide comprises an antibody.

5. The variant of claim 1 wherein the polypeptide comprises a human IgG1 Fc region.

6. The variant of claim 1 which does not activate complement.

7. The variant of claim 6 which binds an FcR.

8. The variant of claim 7 which binds FcγRI, FcγRII, FcγRIII or FcRn.

9. A variant of an antibody or immunoadhesin comprising a human IgG Fc region, which variant binds FcγRI, FcγRII, FcγRIII or FcRn but does not activate complement and comprises an amino acid substitution at amino acid position 322 or amino acid position 329, or both amino acid positions of the human IgG Fc region, where the numbering of the residues in the IgG Fc region is that of the EU index as in Kabat, wherein the antibody variant is able to bind an antigen, and the immunoadhesin variant is able to bind a ligand or receptor.

10. A composition comprising the variant of claim 1 and a physiologically acceptable carrier.

11. A method for modifying an antibody or irmunoadhesin comprising a human IgG Fc region, the method comprising substituting an amino acid residue at amino acid position 270 or 329, or at two or more of amino acid positions 270, 322, 329 and 331 of the human IgG Of region, where the numbering of the residues in the IgG Fc region is that of the EU index as in Kabat, to generate a variant wherein the antibody variant is able to bind an antigen, and the immunoadhesin variant is able to bind a ligand or receptor.

12. A variant of an antibody or immunoadhesin comprising a human IgG Fc region, which variant comprises an amino acid substitution at amino acid position 326, 327, 333 or 334 of the human IgG Fc region, where the numbering of the residues in the IgG Fc region is that of the EU index as in Kabat, wherein the antibody variant is able to bind an antigen, and the immunoadhesin variant is able to bind a ligand or receptor.

13. The variant of claim 12 which comprises amino acid substitutions at two or more of amino acid positions 326, 327, 333 or 334.

14. The variant of claim 13 which comprises amino acid substitutions at three or more amino acid positions 326, 327, 333 or 334.

15. The variant of claim 14 which comprises amino acid substitutions at amino acid positions 326, 327, 333 and 334.

16. A method for modifying an antibody or immunoadhesin comprising a human IgG Fc region, the method comprising substituting an amino acid residue at amino acid position 326, 327, 333 or 334 of the human IgG Fc region, where the numbering of the residues in the IgG Fc region is that of the EU index as in Kabat, to generate a variant wherein the antibody variant is able to bind an antigen, and the immunoadhesin variant is able to bind a ligand or receptor.

17. A variant of an antibody comprising a human IgG Fc region, which variant comprises an amino acid substitution at amiao acid position 270 or 329, or at two or more of amino acid positions 270, 322, 329 and 331 of the human IgG Fc region, where the numbering of the residues in the IgG Fcc region is that of the EU index as in Kabat, wherein the antibody variant binds an antigen.

18. A variant of an antibody comprising a human TgG Fc region, which variant comprises an amino acid substitution at amino acid position 326, 327, 333 or 334 of the human IgG Fc region, where the numbering of the residues in the IgG Fc region is that of the EU index as in Kabat, wherein the antibody variant binds an antigen.

19. The variant of claim 18 wherein the antigen is CD20.

20. The variant of claim 18 wherein the antigen is HER2 receptor.

* * * * *

UNITED STATES PATENT AND TRADEMARK OFFICE
CERTIFICATE OF CORRECTION

PATENT NO.   : 6,528,624 B1                                                              Page 1 of 1
DATED        : March 4, 2003
INVENTOR(S)  : Idusogie et al.

It is certified that error appears in the above-identified patent and that said Letters Patent is hereby corrected as shown below:

Column 47,
Line 19, please delete "Fec" and insert therefor -- Fc --.
Line 52, please delete "irmunoadhesin" and insert therefor -- immunoadhesin --.
Line 56, please delete "Of" and insert therefor -- Fc --.

Column 48,
Line 45, please delete "amiao" and insert therefor -- amino --.
Line 48, please delete "Fec" and insert therefor -- Fc --.
Line 50, please delete "TgG" and insert therefor -- IgG --.

Signed and Sealed this

Fifteenth Day of April, 2003

JAMES E. ROGAN
*Director of the United States Patent and Trademark Office*